United States Patent [19]

Iwakuma et al.

[11] Patent Number: 4,866,196

[45] Date of Patent: Sep. 12, 1989

[54] PHENOXYACETIC ACID DERIVATIVES AND PREPARATION THEREOF

[75] Inventors: Takeo Iwakuma, Ageo; Takayuki Kawaguchi, Tokyo; Toyoharu Yamashita, Kitamoto; Yasuhiko Sasaki, Urawa; Tamotu Shimazaki, Sakado, all of Japan

[73] Assignee: Tanabe Seiyaku Co., Ltd., Japan

[21] Appl. No.: 141,403

[22] Filed: Jan. 4, 1988

Related U.S. Application Data

[63] Continuation of Ser. No. 80,676, Jul. 31, 1987.

[30] Foreign Application Priority Data

Aug. 6, 1986 [JP] Japan ................. 61-184693
Feb. 6, 1987 [JP] Japan ................. 62-26858

[51] Int. Cl.$^4$ .......................................... C07C 143/67
[52] U.S. Cl. ................................................ 560/012
[58] Field of Search ........................ 562/430; 560/12

[56] References Cited

U.S. PATENT DOCUMENTS 4,258,058   3/1981   Witte ................................ 560/12

FOREIGN PATENT DOCUMENTS 0004011   9/1979   European Pat. Off. .
0221344   5/1987   European Pat. Off. .
3000377   9/1981   Fed. Rep. of Germany .
3610643   1/1987   Fed. Rep. of Germany .

Primary Examiner—Paul J. Killos
Attorney, Agent, or Firm—Scully, Scott, Murphy & Presser

[57] ABSTRACT

Novel phenoxyacetic acid of the formula:

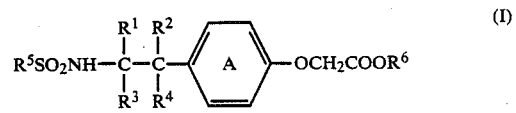

wherein Ring A is phenylene group or a phenylene group having 1 to 2 substituent(s) selected from a lower alkyl group, a lower alkoxy group and a halogen atom; either one or two group(s) of $R^1$, $R^2$, $R^3$ and $R^4$ are a lower alkyl group, and the other groups are hydrogen atom; $R^5$ is phenyl group or a phenyl group having 1 to 3 substituent(s) selected from a lower alkyl group, a halogen atom a lower alkoxy group and nitro group; and —COOR$^6$ is carboxyl group or a protected carboxyl group, or a salt thereof are disclosed. Said derivative (I) and a salt thereof have a potent platelet aggregation-inhibiting activity.

14 Claims, No Drawings

PHENOXYACETIC ACID DERIVATIVES AND PREPARATION THEREOF

This application is a continuation of application Ser. No. 07/080,676 filed 31 July 1987, now abandoned.

This invention relates to a novel phenoxyacetic acid compound and processes for preparing same. More particularly, it relates to a phenoxyacetic acid compound of the formula:

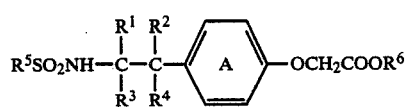

wherein Ring A is phenylene group or a phenylene group having 1 to 2 substituent(s) selected from a lower alkyl group, a lower alkoxy group and a halogen atom; either one or two group(s) of $R^1$, $R^2$, $R^3$ and $R^4$ is/or are a lower alkyl group, and the other groups are hydrogen atom; $R^5$ is phenyl group or a phenyl group having 1 to 3 substituent(s) selected from a lower alkyl group, a halogen atom, a lower alkoxy group, a trihalogenomethyl group and nitro group; and $-COOR^6$ is carboxyl group or a protected carboxyl group, or a salt thereof.

The phenoxyacetic acid compound (I) shows potent platelet aggregation-inhibiting activity and is useful for treatment and/or prophylaxis of thrombotic diseases.

Examples of the compound of the present invention are those of the formula (I) in which Ring A is phenylene group or a phenylene group having 1 to 2 substituent(s) selected from an alkyl group of one to four carbon atoms such as methyl, ethyl, propyl or butyl, an alkoxy group of one to three carbon atoms such as methoxy, ethoxy or propoxy and a halogen atom such as chlorine, bromine or fluorine; either one or two group(s) of $R^1$ to $R^4$ is/or are an alkyl group of one to four carbon atoms such as methyl, ethyl, propyl or butyl, and the other groups of $R^1$ to $R^4$ are hydrogen atom; $R^5$ is phenyl group or a phenyl group having 1 to 3 substituent(s) selected from the class consisting of an alkyl group of one to three carbon atoms such as methyl, ethyl or propyl, a halogen atom such as fluorine, chlorine or bromine, an alkoxy group of one to three carbon atoms such as methoxy, ethoxy or propoxy, a trihalogenomethyl group such as trifluoromethyl group and nitro group; and $-COOR^6$ is carboxyl group which may be optionally protected with a protecting group such as an alkyl group of one to three carbon atoms (e.g., methyl, ethyl or propyl) or a substituted or unsubstituted phenyl-alkyl group of 7 to 13 carbon atoms (e.g., benzyl, p-methoxybenzyl, p-nitrobenzyl or benzhydryl).

Among them, preferred examples of the compound of the invention are those of the formula (I) in which Ring A is phenylene group or a phenylene group having 1 to 2 substituent(s) selected from an alkyl group of one to three carbon atoms, a halogen atom and an alkoxy group of one to three carbon atoms; either one or two group(s) of $R^1$ to $R^4$ are an alkyl group of one to four carbon atoms, and the other groups of $R^1$ to $R^4$ are hydrogen atom; $R^5$ is phenyl group or a phenyl group having 1 to 3 substituent(s) selected from an alkyl group of one to three carbon atoms, a halogen atom, an alkoxy group of one to three carbon atoms, trihalogenomethyl group and nitro group; and $-COOR^6$ is free carboxyl group or a carboxyl group protected with an alkyl group of one to three carbon atoms. Another preferred examples of the compound of the invention are those of the formula (I) in which Ring A is phenylene group or a phenylene group substituted with a halogen atom; either one of $R^1$ to $R^4$ is an alkyl group of one to four carbon atoms, and the other groups of $R^1$ to $R^4$ are hydrogen atom; $R^5$ is phenyl group or a phenyl group substituted with an alkyl group of one to three carbon atoms, a halogen atom, trihalogenomethyl group or nitro group; and $-COOR^6$ is free carboxyl group or a carboxyl group protected with an alkyl group of one to three carbon atoms. Other preferred examples of the compound of the invention are those of the formula (I) in which Ring A is phenylene group or a phenylene group substituted with fluorine atom or chlorine atom; either one of $R^1$ to $R^4$ is methyl group or ethyl group, and the other groups are hydrogen atom; $R^5$ is phenyl group or a phenyl group substituted with methyl group, chlorine atom, bromine atom, trifluoromethyl group or nitro group; and $-COOR^6$ is free carboxyl group or a carboxyl group protected with an alkyl group of one to three carbon atoms.

While the compound (I) of the invention may exist in the form of two optically active isomers or in the form of two stereo isomers or four optically active isomers due to one or two asymmetric carbon atoms, the present invention includes within its scope either one of these isomers and a mixture thereof.

According to the present invention, the compound (I) or a salt thereof can be prepared by the step or steps of:

(i) condensing a phenol compound of the formula:

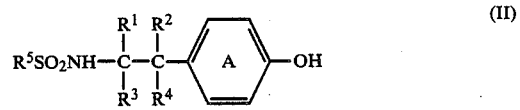

wherein Ring A, $R^1$, $R^2$, $R^3$, $R^4$ and $R^5$ are the same as defined above, or a salt thereof with an acetic acid derivative of the formula:

$$H^1CH_2COOR^{61}$$ (III)

wherein $X^1$ is a reactive residue and $-COOR^{61}$ is carboxyl group or a protected carboxyl group, (ii) when $-COOR^{61}$ is a protected carboxyl group, optionally removing said protecting group therefrom, and (iii) if required, further converting the product into a salt thereof.

Alternatively, the compound (I) or a salt thereof can be prepared by the step or steps:

(i) condensing a phenoxyacetic acid derivative of the formula:

wherein Y is amino group, a protected amino group or a reactive residue, and Ring A, $R^1$, $R^2$, $R^3$, $R^4$ and $-COOR^{61}$ are the same as defined above, or a salt thereof with a benzenesulfonic acid compound of the formula:

$$R^5SO_2Z \tag{V}$$

wherein Z is hydroxy group or a reactive residue when Y is amino group or a protected amino group, or Z is amino group when Y is a reactive residue, and $R^5$ is the same as defined above, (ii) when $-COOR^{61}$ is a protected carboxyl group and/or Y is a protected amino group, optionally removing said protecting group or groups therefrom, and (iii) if required, further converting the product into a salt thereof.

Any protecting groups, which are readily removable by a conventional manner such as hydrolysis, acid-treatment and reduction, may be used to protect the carboxyl group of the starting compound (III) and (IV). Examples of such protecting group (i.e., the group $R^{61}$) include, for example, a lower alkyl group such as methyl, ethyl, propyl or butyl, and a substituted or unsubstituted phenyl-lower alkyl group such as benzyl, p-methoxybenzyl, p-nitrobenzyl or benzhydryl. Examples of the reactive residue $X^1$ and Y or Z include a halogen atom such as chlorine, bromine or iodine, a lower alkylsulfonyloxy group such as methanesulfonyloxy, a substituted or unsubstituted phenyl-sulfonyloxy group such as benzenesulfonyloxy or p-toluenesulfonyloxy, and the like.

The condensation of the starting compounds (II) and (III) can be readily conducted in an inert solvent. Acetone, chloroform, lower alkanols, methylene chloride, tetrahydrofuran, dimethyl sulfoxide, dimethylformamide and a mixture thereof are suitable as the solvent. In carrying out the reaction, the phenol compound (II) may be used in the form of a salt thereof such as an alkali metal salt, an alkaline earth metal salt and the like. It is preferred to carry out the reaction in the presence of an acid acceptor such as an alkali metal carbonate, an alkali metal oxide, an alkali metal bicarbonate and an organic amine (e.g., triethylamine). It is also preferred to carry it out at a temperature of 20° to 100° C.

The condensation of the starting compounds (IV) and (V) can be conducted in the presence of an acid acceptor in or without a solvent. Examples of the acid acceptor include an alkali metal bicarbonate, an alkali metal carbonate, an alkaline earth metal carbonate, and organic bases such as pyridine, trimethylamine or triethylamine. Ether, benzene, methylene chloride, dioxane, ethanol, methanol, water and a mixture thereof are suitable as the solvent. The compound (IV) in which Y is amino group may be used for the reaction in the form of an organic or inorganic acid addition salt such as hydrochloride, hydrobromide, methanesulfonate, oxalate and the like; or the compound (IV) in which Y is a protected amino group and/or $-COOR^{61}$ is free carboxyl group may be used for the reaction in the form of a salt such as an alkali metal salt or an alkaline earth metal salt. Moreover, when Y is a protected amino group, a lower alkanoyl group such as acetyl or propionyl group or an aralkyloxycarbonyl group such as benzyloxycarbonyl group may be preferably used as the protecting group for said amino group. It is preferred to carry out the above-mentioned reaction at a temperature of 50° to 150° C.

When $-COOR^{61}$ is the protected carboxyl group and/or Y is a protected amino group, the subsequent optional removal of said protecting group or groups may be conducted in a conventional manner such as hydrolysis, solvolysis, acid-treatment or reduction.

Since all of the above-mentioned reactions of the invention can be carried out without racemization, the compound in an optically active form can be readily obtained by the use of optical active isomer of the compound (II) or (IV) as the starting compound.

The compound (I) can be used for pharmaceutical use either in the free form or in the form of a salt thereof. Suitable salts of the compound (I) for pharmaceutical use include, for example, pharmaceutically acceptable salts thereof such as alkali metal salts (e.g., sodium salt or potassium salt), alkaline earth metal salts (e.g., calcium salt or magnesium salt), heavy metal salts (e.g., zinc salt), ammonium salt, organic amine salts (e.g., triethylamine salt, pyridine salt or ethanolamine salt), basic amino acid salts (e.g., lysine salt, arginine salt or histidine salt), and the like. These salts can be obtained by treating compound (I) with the stoichiometrically equimolar amount of the corresponding organic or inorganic base.

The compound (I) and a salt thereof may be administered either orally or parenterally and may also be used in the form of a pharmaceutical preparation containing the same compound in admixture with pharmaceutical excipients suitable for oral or parenteral administration. The pharmaceutical preparations may be in solid form such as tablets, capsules or suppositories or in liquid form such as solutions, suspensions or emulsions. Moreover, when administered parenterally, the pharmaceutical preparation may be used in the form of injections.

As mentioned hereinbefore, the compound (I) of the present invention and a salt thereof show potent platelet aggregation-inhibiting activity, and is useful for the treatment, amelioration and/or prophylaxis of a variety of thrombosis or embolism such as cerebral thrombosis, coronary artery thrombosis, pulmonary thrombosis, pulmonary embolism, peripheral vascular embolism, thromboangiitis, and so forth. For example, when the collagen-induced platelet aggregation-inhibiting activity of a test compound is estimated in vitro, (±)-4-[2-(4-chlorophenyl)sulfonylamino-1-methylethyl]phenoxyacetic acid of present invention shows about 4 times as strong a platelet aggregation-inhibiting activity as that of 4-(2-benzenesulfonylaminoethyl)phenoxyacetic acid disclosed in Japanese patent publication (examined) No. 35910/1982. Moreover, the compound (I) and a salt thereof are low in toxity and show a high safety for use as a medicine.

Concomitantly, the starting compound (II) of the present invention may be prepared, for example, by reacting a compound of the formula:

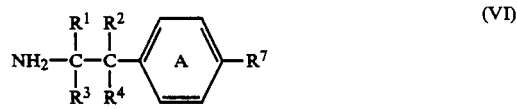

wherein $R^7$ is hydroxy group or a protected hydroxy group and Ring A, $R^1$, $R^2$, $R^3$ and $R^4$ are the same as defined above, with a phenylsulfonyl halide derivative of the formula:

wherein $R^5$ is the same as defined above and $X^2$ is a halogen atom, in the presence of an alkali metal carbonate or organic amine in a solvent, and if required, removing the protecting group from the product obtained above. Alternatively, the starting compound (II) in which either one of $R^2$ and $R^4$ is a lower alkyl group and the other is hydrogen atom and $R^1$ and $R^3$ are hydrogen atom may be prepared by reacting the compound of the formula:

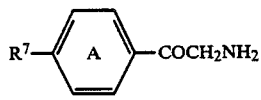
(VIII)

wherein Ring A and $R^7$ are the same as defined above, with the compound (VII) in the presence of an alkali metal carbonate in a solvent, reacting the product with a lower alkyl magnesium halide to give a compound of the formula:

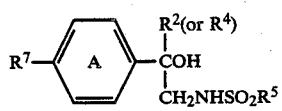
(IX)

wherein Ring A, $R^2$, $R^4$, $R^5$ and $R^7$ are the same as defined above, subjecting the compound (IX) to catalytic hydrogenation in the presence of palladium carbon, and if required, further removing the protecting group therefrom. On the other hand, the starting compound (IV) may be prepared, for example, by reacting a compound of the formula:

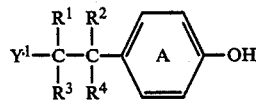
(X)

wherein $Y^1$ is amino group, a protected amino group or a reactive residue and Ring A, $R^1$, $R^2$, $R^3$, and $R^4$ are the same as defined above, with the compound (III) in the presence of an acid acceptor in a solvent, and if requird, removing the protecting group or groups from the product in a conventional manner.

EXPERIMENT 1

Effect on collagen-induced platelet aggregation (in vitro)

Nine volumes of blood collected from a healthy human were mixed with one volume of 3.13% (w/v) trisodium citrate solution, and the mixture was centrifuged to give platelet-rich plasma ("PRP") as the supernatant. The bottom layer was further centrifuged to give platelet-poor plasma ("PPP") as the supernatant. PRP was diluted with PPP so that the platelet count was about $4 \times 10^5$ cells/mm³. 25 μl of a test compound solution containing an equimolar amount of sodium bicarbonate was added to 200 μl of said diluted PRP. After the mixture was stirred for 2 minutes at 37° C., a collagen solution [25–29 μg/ml solution: Biochim. Biophys. Acta, 186, 254 (1969)] was added thereto to induce platelet aggregation. The degree of platelet aggregation was examined by Born's method (Nature, 194, 927 (1962)), and the platelet aggregation-inhibiting activity of the test compound was estimated. The platlet aggregation-inhibiting activity of the test compound was expressed as $IC_{50}$, i.e., the concentration of the test compound required to induce 50% inhibition of collagen-induced platelet aggregation. The results are shown in the following Table 1.

TABLE 1

| Collagen-induced platelet aggregation-inhibiting activity (in vitro) | |
|---|---|
| Test Compounds* | $IC_{50}$(μg/ml) |
| (the compounds of the present invention) | |
| Compound No. 1 | 0.7 |
| Compound No. 2 | 0.5 |
| Compound No. 3 | 0.5 |
| Known Compound | 2 |

*note: chemical name of each test compound.:
Compound No. 1: (±)-4-[2-(4-chlorophenyl)sulfonylaminopropyl] phenoxyacetic acid
Compound No. 2: (±)-4-[2-(4-chlorophenyl)sulfonylamino-1-methylethyl] phenoxyacetic acid
Compound No. 3: (±)-4-[2-(4-bromophenyl)sulfonylamino-1-methylethyl]phenoxyacetic acid
Known Compound: 4-(2-benzenesulfonylaminoethyl)-phenoxyacetica acid (the known compound disclosed in Japanese Patent Publication (examined) No. 35910/1982)

EXPERIMENT 2

Effect on arachidonic acid-induced pulmonary embolism (in vivo)

A test compound (suspended or dissolved in an aqueous sodium bicarbonate and 0.25% carboxymethylcellulose solution) was orally administered to ddy-male mice (5 weeks old, 10 mice per group) fasted overnight. Three hours later, arachidonic acid (125 mg/2.5 ml of 1% $NaHCO_3$ solution+7.5 ml of 0.9% aqueous sodium chloride/kg) was injected to the tail vein of mice to induce pulmonary embolism, and the recovery time(minutes) of locomotive activity of the mice (i.e., the duration from the injection of arachidonic acid to the time the mice recovered from respiratory distress and began to walk) was compared with that of a control group of mice to which an aqueous 0.25% CMC solution was administered instead of the test compound solution. The inhibiting effect of each test compound on arachidonic acid-induced pulmonary embolism was estimated in terms of a minimum effective dose, i.e., the dose required to shorten the recovery time by at least 15% as compared with the control group. The results are shown in the following Table 2.

TABLE 2

| Inhibiting effect on arachidonic acid-induced pulmonary embolism | |
|---|---|
| Test Compounds* | Minimum Effective Dose (mg/kg) |
| (the compounds of the present invention) | |
| Compound No. 1 | 1.0 |
| Compound No. 2 | 0.3 |
| Compound No. 3 | 0.1 |
| Compound No. 4 | 0.1 |
| Compound No. 5 | 0.03 |
| Known Compound | 30 |

*note: chemical name of each test compound:
Compound No. 4: (±)-4-(2-benzenesulfonylamino-1-methylethyl)-2-fluorophenoxyacetic acid
Compound No. 5: (±)-4-(2-(4-chlorophenyl)sulfonylamino-1-methylethyl)-2-fluorophenoxyacetic acid
Compound Nos. 1~3 and Known Compound are the same as mentioned in Experiment 1.

EXPERIMENT 3

Effect on bleeding time (in vivo)

A test compound (suspended or dissolved in an aqueous 0.25% carboxymethylcellulose solution) was orally administered to ddy-male mice (5 weeks old, 10 mice per group) fasted overnight. Three hours later, the tip (ca. 2 mm) of the tail was cut off under ether anesthesia, and said tail was immersed in physiological saline (37° C.) immediately. The bleeding time (seconds) of the medicated group of mice was compared with that of a control group of mice to which an aqueous 0.25% CMC solution was administered instead of the test compound solution. The prolonging effect of each test compound on the bleeding time was estimated in terms of a minimum effective dose, i.e., the dose required to induce at least 50% prolongation of the bleeding time as compared with that of the control group.

Results

In the above-mentioned experiments, the minimum effective dose of Compound Nos. 1, 2 and 3 mentioned in Experiment 1 were 3 mg/kg, 10 mg/kg and 10 mg/kg, respectively, while the minimum effective dose of 4-(2-benzenesulfonylaminoethyl)phenoxyacetic acid disclosed in Japanese patent publication (examined) No. 35910/1982 was 30 mg/kg.

EXAMPLE 1

(1) 4.74 g of 1-benzenesulfonylamino-2-(4-benzyloxyphenyl)-2-propanol are dissolved in a mixture of 100 ml of tetrahydrofuran and 20 ml of water, and 4.29 g of oxalic acid are added thereto. The mixture is subjected to catalytic hydrogenation in the presence of 10% palladium carbon under hydrogen gas atmosphere (3.5 atoms) at 40°-50° C. overnight. After the reaction, the catalyst is filtered off. The filtrate is evaporated under reduced pressure. Ethyl acetate is added to the residue, and the mixture is washed with an aqueous sodium bicarbonate solution and a saturated aqueous sodium chloride solution, successively. The ethyl acetate solution is dried and evaporated under reduced pressure. The residue is recrystallized from a mixture of ethyl acetate and n-hexane, whereby 2.96 g of 4-(1-methyl-2-benzenesulfonylaminoethyl)phenol are obtained as colorless needles.

Yield 85%,
m.p. 162.5°-164° C.

(2) 2.96 g of the product obtained above are dissolved in 25 ml of acetone. 1.54 g of potassium carbonate and 1.87 g of ethyl bromoacetate are added thereto, and the mixture is stirred at room temperature for 6.5 hours. 0.57 g of potassium carbonate and 0.68 g of ethyl bromoacetate are further added thereto and stirred overnight. After the reaction, acetone is evaporated under reduced pressure, and the residue is extracted with ethyl acetate. The extract is washed with water and a saturated aqueous sodium chloride solution, and dried. The ethyl acetate extract is evaporated under reduced pressure, and the residue is purified by column chromatography (solvent; toluene, and toluene:ethyl acetate=20:1 and 10:1), whereby 2.04 g of ethyl 4-(1-methyl-2-benzenesulfonylaminoethyl)phenoxyacetate are obtained as colorless oil.

Yield 53%;
Mass(m/e): 377($M^+$);
IR$\nu_{max}^{neat}$(cm$^{-1}$): 3300, 1750;
NMR(CDCl$_3$,δ): 1.19(3H, t, J=7 Hz), 1.30(3H, d, J=7 Hz), 2.6–3.3(3H, m), 4.28(2H, q, J=7 Hz), 4.59(2H, s), 6.7–7.9(9H, m).

(3) 1.55 g of the product obtained above are dissolved in 16 ml of ethanol. 6.2 ml of a 1N-aqueous sodium hydroxide solution are added thereto, and the mixture is stirred at room temperature for 2 hours. The mixture is evaporated under reduced pressure, and the residue is dissolved in 6 ml of water, and passed through a column packed with a non-ionic adsorption resin (manufactured by Mitsubishi Chemical Industries Ltd. under the trade mark "HP-20", hereinafter referred to as "HP-20"). The column is washed with water and eluted with an aqueous 50% methanol solution. The fractions containing the desired product are collected and evaporated to remove the solvent. Isopropyl alcohol is added to the residue, whereby 1.13 g of sodium 4-(1-methyl-2-benzenesulfonylaminoethyl)phenoxyacetate are obtained as colorless powder.

Yield 74%;
M.p. 180° C.;
Mass (m/e): 394($M^+$+Na), 372($M^+$+H);
IR$\nu_{max}^{nujol}$(cm$^{-1}$): 3280;
NMR(D$_2$O,δ): 1.11(3H, d, J=7 Hz), 2.6–3.1(3H, m), 4.43(2H, s), 6.7–7.1(4H, m), 7.4–7.8(5H, m);
Free carboxylic acid: colorless caramel;
Mass(m/e): 349($M^+$), 179;
IR$_{max}^{CHCl_3}$(cm$^{-1}$): 1740;
NMR(CDCl$_3$,δ): 1.19(3H, d, J=6.5 Hz), 2.86–3.29(3H, m), 4.63(2H, s), 6.67–7.83(9H, m).

EXAMPLE 2

(1) 11.13 g of dl-4-(2-aminopropyl)phenol hydrobromide are added to a mixture of 3.18 g of sodium carbonate, 100 ml of ethyl acetate and 100 ml of water. A solution of 9.71 g of benzenesulfonyl chloride in 50 ml of ethyl acetate and a solution of 3.18 g of sodium carbonate in 30 ml of water are added dropwise to said mixture at 0°-5° C. under stirring. After the mixture is stirred at 10° C. for 0.5 hour, the mixture is neutralized with 10% hydrochloric acid. The organic layer is separated therefrom, and the aqueous layer is extracted with chloroform. The above-obtained organic layer and the chloroform extract are mixed, and the mixture is evaporated under reduced pressure to remove the solvent. The residue is recrystallized from n-hexane, whereby 7.48 g of dl-4-(2-benzenesulfonylaminopropyl)phenol are obtained as colorless prism.

Yield 86%;
m.p. 97°-99° C.;
Mass (m/e): 291($M^+$);
IR $\nu_{max}^{nujol}$(cm$^{-1}$): 3480, 3440, 3340, 3300
NMR(CDCl$_3$+D$_2$O,δ): 1.08(3H, d, J=6 Hz), 2.59(2H, d, J=6 Hz), 3.23–3.72(1H, m), 6.67(2H, d, J=9 Hz), 6.84(2H, d, J=9 Hz), 7.3–7.57(3H, m), 7.6–7.8(2H, m).

(2) 7.4 g of the product obtained above and 3.51 g of potassium carbonate are added to 140 ml of acetone. A solution of 4.66 g of ethyl bromoacetate in 10 ml of acetone is added thereto, and the solution is stirred at room temperature for 18 hours. After the reaction, the solution is condensed to a volume of about 50 ml under reduced pressure, neutralized with 10% ethanolic hydrochloric acid, and extracted with chloroform. The chloroform extract is evaporated under reduced pressure, and the residue is purified by silica gel column chromatography (solvent; chloroform:methanol=50:1 and 20:1), whereby 8.50 g of ethyl dl-4-(2-benzenesulfonylaminopropyl)phenoxyacetate are obtained as colorless oil.

Yield 83.5%;
Mass (m/e): 377($M^+$);
IR $\nu_{max}^{neat}$(cm$^{-1}$): 3270, 1745.

(3) 8.5 g of the product obtained above are added to 100 ml of a 10% aqueous sodium hydroxide solution.

The solution is stirred at 100° C. for 5 minutes and at room temperature of 0.5 hour, and then adjusted to pH 3 with conc. hydrochloric acid. The solution is extracted with chloroform. The extract is dried and evaporated under reduced pressure, whereby 6.88 g of dl-4-(2-benzenesulfonylaminopropyl)phenoxyacetic acid are obtained as colorless powder.

Yield 87%;
m.p. 131°–132° C. (recrystallized from the mixture of acetone and n-hexane);
Mass (m/e): 394(M+);
IR $\nu_{max}^{nujol}$(cm$^{-1}$): 3285, 1730;
NMR(CDCl$_3$+D$_2$O,δ): 1.06(3H, d, J=7 Hz), 2.61(2H, d, J=7 Hz), 3.20–3.75(1H, m), 4.55(2H, s), 6.77(2H, d, J=9 Hz), 6.93(2H, d, J=9 Hz), 7.22–7.60(3H, m), 7.63–7.82(2H, m).

Sodium salt: colorless powder (recrystallized from ethanol
m.p. 192°–194° C.;
Mass (m/e): 394(M++Na), 372(M++H);
IR $\nu_{max}^{nujol}$(cm$^{-1}$): 3290, 1615;
NMR(DMSO-d$_6$,δ): 0.85(3H, d, J=6.5 Hz), 2.24–2.70(2H, m), 3.04–3.54(1H, m), 3.40(1H, s), 4.10(2H, s), 6.70(2H, d, J=9 Hz), 6.88(2H, d, J=9 Hz), 7.40–7.90(5H, m).

EXAMPLE 3

(1) 5.043 g of (R)-1-(4-methoxyphenyl)-2-aminopropane and 8.40 g of sodium bicarbonate are added to a mixture of 50 ml of methylene chloride and 50 ml of water. A solution of 4.86 g of benzenesulfonyl chloride in methylene chloride are added dropwise to the mixture at 5° to 10° C. and stirred at room temperature for b 2 hours. After the reaction, the methylene chloride layer is separated therefrom, and the aqueous layer is extracted with methylene chloride. The methylene chloride solutions are combined, dried and evaporated under reduced pressure. The residue is purified by silica gel column chromatography (solvent; chloroform, and chloroform:methanol=50:1) and recrystallized from a mixture of isopropylether and methanol, whereby 6.76 g of (R)-1-(4-methoxyphenyl)-2-benzenesulfonylaminopropane are obtained as colorless prism.

Yield 88.6%;
m.p. 75°–75.50° C.;
$[\alpha]_D^{20}$ −18.84° (C=1.072, methanol)

(2) A solution of 14.3 g of boron tribromide in 20 ml of methylene chloride is added dropwise to 120 ml of methylene chloride containing 6.10 g of the product obtained above. Said dropwise addition is carried out in argon gas atmosphere at −78° C. After the solution is allowed to stand at room temperature for 1.5 hours, 20 ml of water are added thereto under cooling. The methylene chloride layer is separated therefrom, washed with a saturated aqueous sodium chloride solution, dried and evaporated under reduced pressure. The residue is recrystallized from a mixture of chloroform and isopropylether, whereby 5.59 g of (R)-4-(2-benzenesulfonylaminopropyl)phenol are obtained as colorless plates.

Yield 96.1%
m.p. 92°–92.50° C.
$[\alpha]_D^{20}$ −22.50° (C=1.00, methanol)

(3) 5.24 g of the product obtained above, 3.31 g of ethyl bromoacetate and 2.49 g of potassium carbonate are added to 150 ml of acetone, and the solution is stirred at room temperature for 19 hours. 0.6 g of ethyl bromoacetate is further added thereto. After stirring for 8 hours, inorganic materials are filtered off, and the filtrate is evaporated under reduced pressure. The residue is purified by silica gel column chromatography (solvent; chloroform:methanol=100:1), and recrystallized from a mixture of chloroform and isopropylether, whereby 5.05 g of ethyl (R)-4-(2-benzenesulfonylaminopropyl)phenoxyacetate are obtained as colorless needles.

Yield 74.3%;
m.p. 108.5°–109° C.;
$[\alpha]_D^{20}$ −11.03° (C=1.015, methanol);
IR $\nu_{max}^{nujol}$(cm$^{-1}$): 3300, 1750;
Mass (m/e): 377(M+).

(4) 4.68 g of the product obtained above are dissolved in a mixture of 1 g of sodium hydroxide, 80 ml of tetrahydrofuran and 10 ml of water. The mixture is stirred at room temperature for 1.5 hours. After the reaction, tetrahydrofuran is evaporated under reduced pressure. The residue is made acidic with 10% hydrochloric acid and extracted with chloroform. The chloroform extract is washed with a saturated aqueous sodium chloride solution, dried and evaporated under reduced pressure. The residue is recrystallized from a mixture of isopropylether and methylene chloride, whereby 4.2 g of (R)-4-(2-benzenesulfonylaminopropyl)phenoxyacetic acid are obtained as colorless needles.

Yield 97%;
m.p. 92°–93° C.;
$[\alpha]_D^{20}$ −12.01° (C=1.074, methanol);
IR $\nu_{max}^{nujol}$(cm$^{-1}$): 3315, 3215, 1740, 1705.

The Mass and NMR data of this product are identical with those of the product obtained in Example 2-(3).

Sodium salt: colorless powder (recrystallized from ethanol)
m.p. 193°–196° C.;
$[\alpha]_D^{20}$ −15.41° (C=1.012, methanol).

EXAMPLE 4

(1) (S)-1-(4-methoxyphenyl)-2-aminopropane is treated in the same manner as described in Example 3-(1), whereby (S)-1-(4-methoxyphenyl)-2-benzenesulfonylaminopropane is obtained.

Yield 94.2%;
m.p. 74.5°–76° C.;
$[\alpha]_D^{20}$ +18.60° (C=1.00, methanol).

(2) The product obtained above is treated in the same manner as described in Example 3-(2), whereby (S)-4-(2-benzenesulfonylaminopropyl)phenol is obtained.

Yield 90.2%;
m.p. 92°–94° C.;
$[\alpha]_D^{20}$ +22.00° (C=1.00, methanol).

(3) The product obtained above is treated in the same manner as described in Example 3-(3), whereby ethyl (S)-4-(2-benzenesulfonylaminopropyl)phenoxyacetate is obtained.

Yield 75%;
m.p. 109°–110.5° C.;
$[\alpha]_D^{20}$ +10.50° (C=1.00, methanol).

(4) The product obtained above is treated in the same manner as described in Example 3-(4), whereby (S)-4-(2-benzenesulfonylaminopropyl)phenoxyacetic acid is obtained.

Yield 99%;
m.p. 89°–91° C.;
$[\alpha]_D^{20}$ +11.90° (c=1.008, methanol);
IR $\nu_{max}^{nujol}$(cm$^{-1}$): 3315, 3215, 1740, 1705.

The Mass and NMR data of this product are identical with those of the product obtained in Example 2-(3).

Sodium salt: colorless powder (recrystallized from ethanol)
m.p. 192°–195° C.);
$[\alpha]_D^{20} + 15.13°$ (C=1.004, methanol).

EXAMPLE 5

(1) A mixture of 2.32 g of (±)-4-(2-aminopropyl)-phenol hydrobromide, 4.2 g of sodium bicarbonate, 50 ml of water, 100 ml of ethyl acetate and 2.06 g of 4-methoxyphenylsulfonyl chloride is stirred at room temperature for 3 hours. After the reaction, the ethyl acetate layer is separated therefrom, dried and evaporated to remove the solvent, whereby 2.4 g of (±)-4-[2-(4-methoxyphenyl)sulfonylaminopropyl)phenol are obtained as brown oil.
Yield 75%;
m.p. 119°–120.5° C.(recrystallization from n-hexane),
IR $\nu_{max}^{nujol}$(cm$^{-1}$): 3420, 3260.

(2) A mixture of 2.37 g of the product obtained above, 1.21 g of methyl bromoacetate, 1 g of potassium carbonate and 30 ml of acetone is stirred at room temperature for 24 hours. After the reaction, acetone is distilled off. Water is added to the residue, and the mixture is extracted with ethyl acetate. The extract is evaporated to remove ethyl acetate under reduced pressure. Methyl (±)-4-[2-(4-methoxyphenyl)sulfonylaminopropyl]-phenoxyacetate obtained as the crude product is dissolved in 30 ml of methanol, and 15 ml of a 10% aqueous sodium hydroxide solution are added thereto. The mixture is allowed to stand at room temperature for 1 hour. Then, the mixture is made acidic with 10% hydrochloric acid, and extracted with chloroform. The extract is dried and evaporated to remove the solvent. The residue is purified by silica gel column chromatography (solvent; chloroform, and chloroform:methanol=19:1), whereby 2.01 g of (±)-4-[2-(4-methoxphenyl)sulfonylaminopropyl)phenoxyacetic acid are obtained as oil.
Yield 77%;
Mass(m/e): 379(M+);
IR $\nu_{max}^{CHCl_3}$(cm$^{-1}$): 3680, 1738;
NMR(CDCl$_3$,δ): 1.06 (3H, d, J=7.3 Hz), 2.58(2H, d, J=6.6 Hz), 3.83(3H, s), 3.2–3.6(1H, m), 4.60(2H, s), 6.6–7.0(6H, m), 7.61(2H, d, J=9 Hz).

(3) 1.7 g of the product obtained above is dissolved in 10 ml of methanol, and 5 ml of a 1N-aqueous sodium hydroxide solution are added thereto. The solution is evaporated to remove the solvent. The residue is dissolved in 10 ml of water, purified by column chromatography, and recrystallized from a mixture of isopropyl alcohol and water, whereby 1.43 g of sodium (±)-4-[2-(4-methoxyphenyl)sulfonylaminopropyl]phenoxyacetate are obtained as colorless granules.
m.p. 177°–179° C.
Mass(m/e): 424(M+ +Na), 402(M+ +H)
NMR (D$_2$O,δ): 1.14(3H, t, J=6 Hz), 2.38(1H, d,d, J=14 Hz, J=9 Hz), 2.62(1H, d,d, J=14 Hz, J=5.5 Hz), 3.1–3.5(1H, m), 3.84(3H, s), 4.39(2H, s), 6.62(2H, d, J=9 Hz), 6.85(2H, d, J=8 Hz), 6.86(2H, d, J=9 Hz), 7.44(2H, d, J=8 Hz).

EXAMPLE 6

(1) A mixture of 2.69 g of (±)-1-(4-methoxyphenyl)-2-aminobutane, 6.3 g of sodium bicarbonate, 60 ml of water, 120 ml of ethyl acetate and 2.65 g of benzenesulfonyl chloride is stirred at room temperature for 3 hours. After the reaction, the ethyl acetate layer is separated therefrom, dried and evaporated under reduced pressure. The oily residue thus obtained is dissolved in 50 ml of methylene chloride. A solution of 9.02 g of boron tribromide in 10 ml of methylene chloride are added dropwise thereto at a temperature of −50° to −60° C. The mixture is stirred at room temperature for 2 hours. After the reaction, the mixture is cooled, excess boron tribromide is decomposed with water, and 50 ml of chloroform are added thereto. The organic layer is separated therefrom, dried and evaporated to remove the solvent. The residue is purified by silica gel column chromatography (solvent; ethyl acetate:n-hexane=1:9 to 1:3), whereby 3.70 g of (±)-4-(2-benzenesulfonylaminobutyl)phenol are obtained as pale yellow oil.
Yield 81%;
Mass (m/e): 305(M+);
IR $\nu_{max}^{CHCl_3}$(cm$^{-1}$): 3600, 3380, 1608.

(2) The product obtained above is treated in the same manner as described in Example 5-(2) to give (±)-4-(2-benzenesulfonylaminobutyl)phenoxyacetic acid as oil.
Yield 68%;
IR $\nu_{max}^{CHCl_3}$(cm$^{-1}$): 3380, 1738.

EXAMPLES 7–20

(1) The corresponding starting compounds are treated in the same manner as described in Example 5-(1) or 6-(1) to give the compounds shown in Table 3 (In the following Tables, (+) and (−) express the optical activity of each compound obtained).

TABLE 3

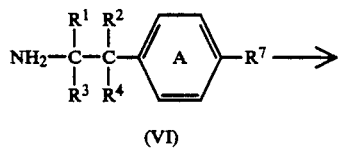

(VI)

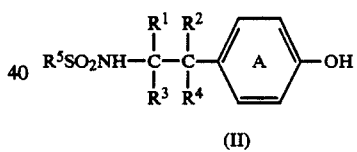

(II)

(part 1) (Ring A = p-phenylene group, $R^1$ = H, $R^2$ = H, $R^7$ = OH in Example 7, 9 and 10, and $R^7$ = OCH$_3$ in Example 8 and 11 to 19)

| Ex. Nos. | Compound(II) | | | Yield M.p. |
|---|---|---|---|---|
| | $R^5$ | $R^3$ | $R^4$ | |
| 7 | Cl—⌬— | CH$_3$ | H | 100%, oil |
| 8 | F—⌬— | CH$_3$ | H | 99%, oil |
| 9 | Cl—⌬— | n-C$_4$H$_9$ | H | 68%, oil |
| 10 | ⌬— | H | C$_2$H$_5$ | 78% 115–116° C. |

TABLE 3-continued

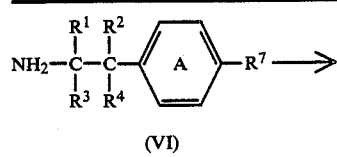

(VI)

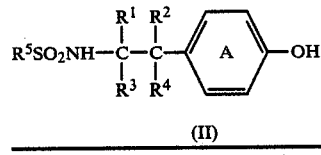

(II)

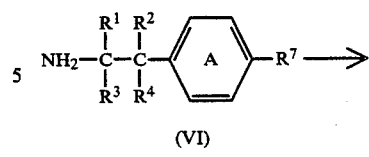

(VI)

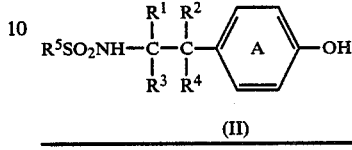

(II)

| Ex. No. | $R^5$ | $R^3$ | $R^2$ and $R^4$ | Yield M.p. |
|---|---|---|---|---|
| 11 | phenyl | H | n-$C_3H_7$ | 75% 110–111.5° C. |
| 12 | phenyl | H | n-$C_4H_9$ | 74% 123.5–124.5° C. |
| 13 | phenyl | H | i-$C_3H_7$ | 76% 123.5–124.5° C. |
| 14 | phenyl | H | $CH_3$ (−) | 61% 172°–172.5° C. |
| 15 | phenyl | H | $CH_3$ (+) | 59% 172–172.5° C. |
| 16 | 4-Cl-phenyl | $CH_3$ (−) | H | 80% 108–108.5° C. |
| 17 | 4-Cl-phenyl | $CH_3$ (+) | H | 78% 108–108.5° C. |
| 18 | 4-Br-phenyl | H | $CH_3$ (−) | 94% 14 224.5° C. |
| 19 | 4-Br-phenyl | H | $CH_3$ (+) | 93% 223.5–225° C. |

(part 2) (Ring A = phenylene group, $R^1$ = H, $R^7$ = $OCH_3$)

| Ex. No. | $R^5$ | $R^3$ | $R^2$ and $R^4$ | Yield M.p. |
|---|---|---|---|---|
| 20 | phenyl | H | $CH_3$ | 87% 135–136° C. |

(2) The corresponding starting compounds are treated in the same manner as described in Example 5-(2), whereby the compounds shown in Table 4 are obtained.

TABLE 4

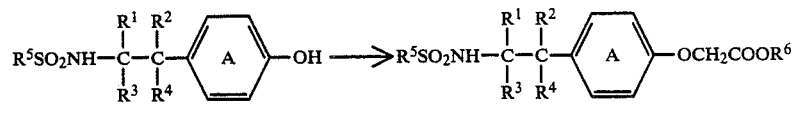

(II)                                      (I)

(part 1) (Ring A = phenylene group, $R^1$ = H, $R^2$ = H, $R^6$ = H)

| Ex. Nos. | $R^5$ | $R^3$ | $R^4$ | Compound(I) Yield M.p. (recrystallization solvent) IR and/or optical rotation |
|---|---|---|---|---|
| 7 | 4-Cl-phenyl | $CH_3$ | H | 50% 132–136° C. (chloroform-n-hexane) IR $\nu_{max}^{nujol}$ (cm$^{-1}$): 3340, 3260, 1780 |
| 8 | 4-F-phenyl | $CH_3$ | H | 72% 134–137° C. (ethyl acetate-n-hexane) IR $\nu_{max}^{nujol}$ (cm$^{-1}$): 3290, 1730 |

TABLE 4-continued $$R^5SO_2NH-\underset{R^3}{\underset{|}{\overset{R^1}{\overset{|}{C}}}}-\underset{R^4}{\overset{R^2}{\overset{|}{C}}}-\underset{}{\boxed{A}}-OH \longrightarrow R^5SO_2NH-\underset{R^3}{\underset{|}{\overset{R^1}{\overset{|}{C}}}}-\underset{R^4}{\overset{R^2}{\overset{|}{C}}}-\underset{}{\boxed{A}}-OCH_2COOR^6$$

(II) → (I)

| Ex. No. | R⁵ | R³ | R⁴ | Yield, properties |
|---|---|---|---|---|
| 9 | 4-Cl-C₆H₄- | n-C₄H₉ | H | 73%, oil<br>IR $\nu_{max}^{CHCl_3}$ (cm⁻¹): 1730 |
| 10 | C₆H₅- | H | C₂H₅ | 71%, oil<br>IR $\nu_{max}^{neat}$ (cm⁻¹): 3280,1730 |
| 11 | C₆H₅- | H | n-C₃H₇ | 63%, oil<br>IR $\nu_{max}^{neat}$ (cm⁻¹): 3280,1730 |
| 12 | C₆H₅- | H | n-C₄H₉ | 59%, oil<br>IR $\nu_{max}^{neat}$ (cm⁻¹): 3280,1730 |
| 13 | C₆H₅- | H | i-C₃H₇ | 64%<br>137–138° C. (ethyl acetate-n-hexane)<br>IR $\nu_{max}^{nujol}$ (cm⁻¹): 3300,1740 |
| 14 | C₆H₅- | H | CH₃ (−) | 50%, oil<br>$[\alpha]_D^{20}$ −11.26° (C = 1.039, methanol) |
| 15 | C₆H₅- | H | CH₃ (+) | 51%, oil<br>$[\alpha]_D^{20}$ +11.10° (C = 1.020, methanol) |
| 16 | 4-Cl-C₆H₄- | CH₃ (−) | H | 60%<br>132–133° C. (ethyl acetate-n-hexane)<br>IR $\nu_{max}^{nujol}$ (cm⁻¹): 3300,3275, 1725,1700<br>$[\alpha]_D^{20}$ −17.33° (C = 1.027, methanol) |
| 17 | 4-Cl-C₆H₄- | CH₃ (+) | H | 52%<br>132.5–133° C. (isopropylether-chloroform)<br>IR $\nu_{max}^{nujol}$ (cm⁻¹): 3300,3275, 1725,1700<br>$[\alpha]_D^{20}$ +17.47° (C = 1.007, methanol) |
| 18 | 4-Br-C₆H₄- | H | CH₃ (−) | 149.5–150° C. (isopropylalchohol-chloroform)<br>$[\alpha]_D^{20}$ −7.84° (C = 0.790, methanol) |
| 19 | 4-Br-C₆H₄- | H | CH₃ (+) | 150.5–152° C. (isopropylalcohol-chloroform)<br>$[\alpha]_D^{20}$ +8.07° (C = 1.016, methanol) |

(part 2) (Ring A = phenylene group, R¹ = H, R⁶ = H)

| Ex. No. | R⁵ | R³ | R² and R⁴ | Yield IR |
|---|---|---|---|---|

TABLE 4-continued

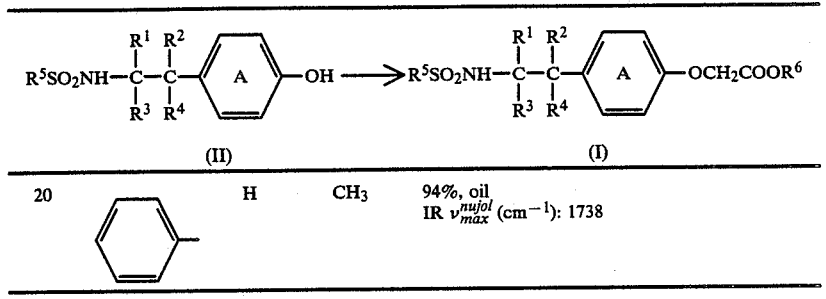

| 20 | ⌬ | H | CH₃ | 94%, oil |
| --- | --- | --- | --- | --- |
| | | | | IR $\nu_{max}^{nujol}$ (cm$^{-1}$): 1738 |

Sodium salt of the compound of Ex. No. 9: m.p. 187°–188° C.

EXAMPLE 21

(1) A mixture of 4.72 g of (±)-4-(2-benzyloxycarbonylamino-1-methylethyl)phenol, 2.53 g of methyl bromoacetate, 50 ml of acetone and 3.43 g of potassium carbonate is stirred at room temperature overnight. After the reaction, the mixture is evaporated to remove acetone, and water is added to the residue. The aqueous mixture is extracted with chloroform, and then the extract is dried and evaporated under reduced pressure, whereby 5.68 g of methyl (±)-4-(2-benzyloxycarbonylamino-1-methylethyl)phenoxyacetate are obtained as oil.

Yield 96%;
Mass (m/e): 357(M+);
IR $\nu_{max}^{neat}$(cm$^{-1}$): 3200–3500, 1755, 1712.

(2) 5.36 g of the product are dissolved in 60 ml of methanol, and 2 ml of conc. hydrochloric acid are added thereto. The mixture is subjected to catalytic hydrogenation in the presence of 0.6 g of 10% palladium carbon at room temperature under an atmospheric pressure. After the reaction, the catalyst is filtered off, and the filtrate is evaporated under reduced pessure. The residue is recrystallized from a mixture of isopropylalcohol and ether, whereby 3.06 g of methyl (±)-4-(2-amino-1-methylethyl)phenoxyacetate hydrochloride are obtained as colorless crystals.

Yield 79%;
m.p. 99°–104° C.
Mass (m/e): 223 (M+);
IR $\nu_{max}^{nujol}$ (cm$^{-1}$): 2400–2800, 1732.

(3) A mixture of 1.82 g of the product obtained above, 50 ml of ethyl acetate, 1.76 g of sodium bicarbonate, 30 ml of water and 1.53 g of 2,4,6-trimethylphenylsulfonyl chloride is stirred at a temperature of 5° to 10° C. for 2.5 hours. After the reaction, the ethyl acetate layer is separated therefrom, dried and evaporated under reduced pressure. Methyl (±)-4-[2-(2,4,6-trimethylphenyl(sulfonylamino-1-methylethyl]phenoxyacetate obtained as the crude product is dissolved in 20 ml of methanol, and 8 ml of a 1N-aqueous sodium hydroxide solution are added thereto. The mixture is allowed to stand for 1 hour. Then, the mixture is evaporated to remove ethanol, neutralized with 5% hydrochloric acid, and extracted with chloroform. The chloroform extract is dried and evaporated to remove the solvent, whereby 1.6 g of (±)-4-[2-(2,4,6-trimethylphenyl)sulfonylamino-1-methylethyl]phenoxyacetic acid are obtained as viscous oil.

Yield 59%;
Mass (m/e): 391 (M+);
IR $\nu_{max}^{CHCl_3}$(cm$^{-1}$): 1735, 1600;
H¹-NMR (CDCl₃, δ): 1.17 (3H, d, J=6.4 Hz), 2.30 (3H, s), 2.48 (6H, s), 2.6–3.2 (3H, m), 4.65 (2H, s), 6.80 (2H, d, J=9 Hz), 6.91 (2H, s), 6.98 (2H, d, J=9 Hz).

EXAMPLE 22–24

(1) The corresponding starting compounds are treated in the same manner as described in Example 21-(1) and (2) to give the compounds shown in Table 5.

TABLE 5

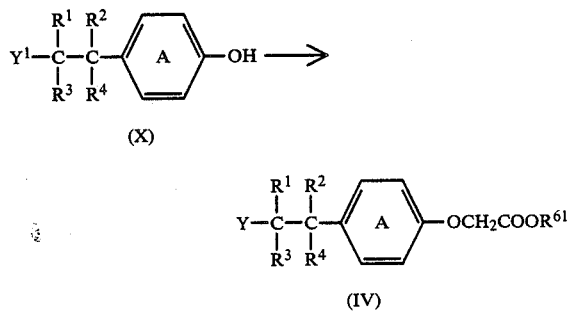

(Ring A = phenylene group, R¹ = H, R² = H, R= CH₃,

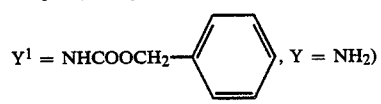

Y¹ = NHCOOCH₂— , Y = NH₂)

| Ex. Nos. | R³ | R⁴ | Compound(IV) Yield M.p. |
| --- | --- | --- | --- |
| 22 | CH₃ | H | 81% |
| | | | 123.5–125° C. (hydrochloride) |
| 23 | C₂H₅ | H | 60% |
| | | | 138–139° C. (hydrochloride) |
| 24 | H | C₂H₅ | 59% |
| | | | 98–100° C. (oxalate) |

(2) The corresponding starting compounds are treated in the same manner as described in Example 21-(3) to give the compounds shown in Table 6.

TABLE 6

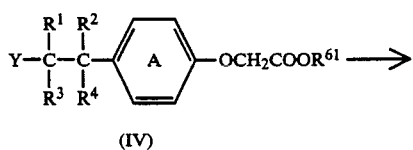
(IV)

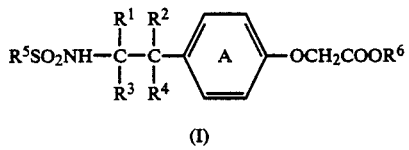
(I)

(Ring A = phenylene group, $R^1$ = H, $R^2$ = H, $R^6$ = H, $R^{61}$ = H, Y = $NH_2$)

| Ex. Nos. | $R^5$ | $R^3$ | $R^4$ | Compound (II) Yield, M.p., IR |
|---|---|---|---|---|
| 22 | Br—⟨phenyl⟩— | $CH_3$ | H | 95%<br>140.5–142° C. (ethyl acetate-n-hexane)<br>IR $\nu_{max}^{nujol}$ (cm$^{-1}$): 3290, 1730 |
| 23 | Cl—⟨phenyl⟩— | $C_2H_5$ | H | 86%<br>126–128° C. (ethyl acetate-n-hexane)<br>IR $\nu_{max}^{nujol}$ (cm$^{-1}$): 3270, 3180, 1780 |
| 24 | Cl—⟨phenyl⟩— | H | $C_2H_5$ | 100%, oil<br>IR $\nu_{max}^{CHCl_3}$ (cm$^{-1}$): 1735 |

Sodium salt of the compound of Ex. No. 22: m.p. 216–219.5° C.

EXAMPLES 25 TO 33

The corresponding starting compounds are treated in the same manner as described in Example 21 to give the compounds shown in Table 7.

TABLE 7

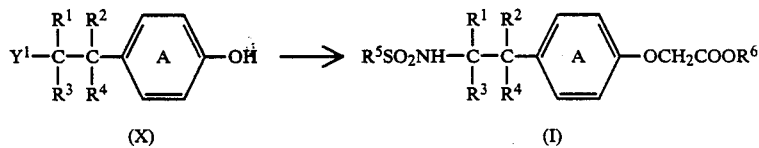

(Ring A = phenylene group, $R^1$ = H, $R^2$ = H, $R^6$ = H, $Y^1$ = NHCOOCH$_2$—⟨phenyl⟩)

| Ex. Nos. | $R^5$ | $R^3$ | $R^4$ | Compound (I)<br>Yield<br>M.p. (recrystallization solvent)<br>IR and/or optical rotation |
|---|---|---|---|---|
| 25 | $NO_2$—⟨phenyl⟩— | H | $CH_3$ | 100%, oil<br>IR $\nu_{max}^{CHCl_3}$ (cm$^{-1}$): 1730 |
| 26 | $NO_2$—⟨phenyl⟩— | $CH_3$ | H | 93%<br>178–179° C. (ethyl acetate-n-hexane)<br>IR $\nu_{max}^{nujol}$ (cm$^{-1}$): 3280, 1730 |

TABLE 7-continued

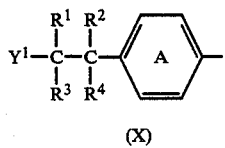

| Ex. No. | (structure) | R³ | R⁴ | Yield, M.p., IR |
|---|---|---|---|---|
| 27 | 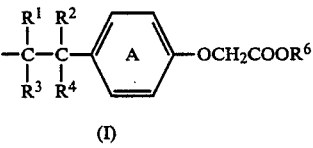 2-Cl-phenyl | H | CH₃ | 100%, oil<br>IR $\nu_{max}^{neat}$ (cm⁻¹): 3300, 1730 |
| 28 | 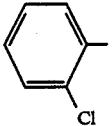 2-Cl-phenyl | CH₃ | H | 100%, oil<br>IR $\nu_{max}^{neat}$ (cm⁻¹): 3300, 1730 |
| 29 | 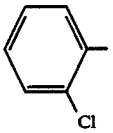 2-CH₃-3-Cl(?) phenyl | H | CH₃ | 100%, oil<br>IR $\nu_{max}^{neat}$ (cm⁻¹): 3320, 1735 |
| 30 | 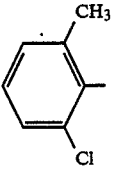 4-F-3-Cl-phenyl | H | CH₃ | 100%, oil<br>IR $\nu_{max}^{CHCl_3}$ (cm⁻¹): 3500, 3300, 1735 |
| 31 | 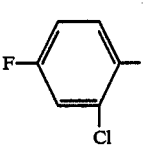 4-CF₃-3-Cl-phenyl | H | CH₃ | 100%, oil<br>IR $\nu_{max}^{neat}$ (cm⁻¹): 3320, 1730 |
| 32 | 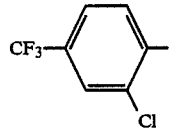 2,4-Cl₂-phenyl | H | CH₃ | 100%, oil<br>IR $\nu_{max}^{CHCl}$ (cm⁻¹): 3500, 3380, 1735 |
| 33 | 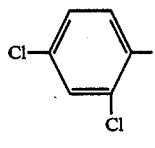 4-CF₃-phenyl | H | CH₃ | 100%<br>99–102° C. (decomp. ethyl acetate-n-hexane)<br>IR $\nu_{max}^{nujol}$ (cm⁻¹): 3280, 1730, 1710 |

($R^1 = H, R^2 = CH_3, R^3 = H, R^4 = H, R^7 = OCH_3$)

Compound (I)

| Ex. Nos. | R⁵ | 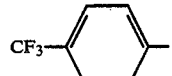 —OCH₂COOR⁶ | Yield<br>M.p. (recrystallization solvent)<br>IR and/or optical rotation |
|---|---|---|---|
| 34 |  phenyl | 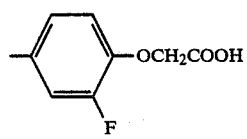 3-F-phenyl-OCH₂COOH | 90%<br>49–51° C. (isopropylalchohol-water)<br>IR $\nu_{max}^{nujol}$ (cm⁻¹): 1740 |

TABLE 7-continued $$Y^1-\underset{\underset{R^3}{|}}{\overset{\overset{R^1}{|}}{C}}-\underset{\underset{R^4}{|}}{\overset{\overset{R^2}{|}}{C}}-\underset{(X)}{\overset{}{\text{A}}}-OH \longrightarrow R^5SO_2NH-\underset{\underset{R^3}{|}}{\overset{\overset{R^1}{|}}{C}}-\underset{\underset{R^4}{|}}{\overset{\overset{R^2}{|}}{C}}-\underset{(I)}{\overset{}{\text{A}}}-OCH_2COOR^6$$

| No. | Y¹-C(R¹)(R³)- group | A-OCH₂COOR⁶ group | Yield / Properties |
|---|---|---|---|
| 35 | 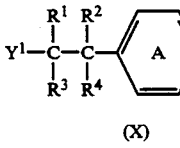 | 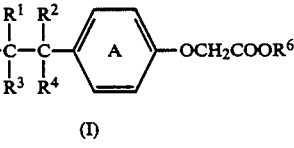 | 90%<br>106.5–108.5° C. (ethyl acetate-n-hexane)<br>IR $\nu_{max}^{nujol}$ (cm$^{-1}$): 1740 |
| 36 | 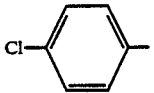 | 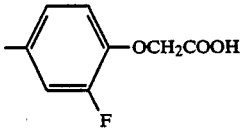 | 93%, oil<br>IR $\nu_{max}^{nujol}$ (cm$^{-1}$): 1740 |
| 37 | 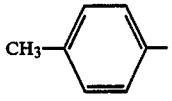 | 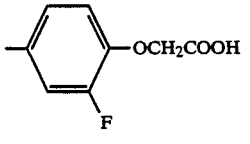 | 70%<br>104–105° C. (isopropylalchohol-water)<br>IR $\nu_{max}^{nujol}$ (cm$^{-1}$): 1720 |
| 38 | 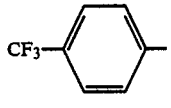 | 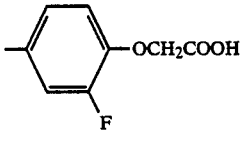 | 62%<br>138–140° C. (ethyl acetate-n-hexane)<br>IR $\nu$hd max$^{nujol}$ (cm$^{-1}$): 1740 |
| 39 | 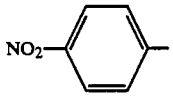 | 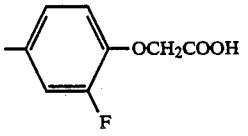 | 96%<br>105–106° C. (isopropylalchohol-water)<br>IR $\nu_{max}^{nujol}$ (cm$^{-1}$): 1730 |
| 40 | 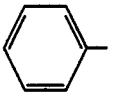 | 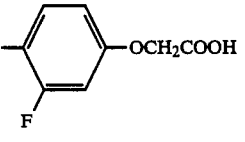 | 96%, oil<br>IR $\nu_{max}^{neat}$ (cm$^{-1}$): 1740 |
| 41 | 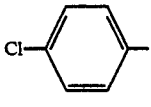 | 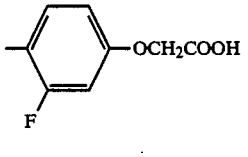 | 95%, oil<br>IR $\nu_{max}^{neat}$ (cm$^{-1}$): 1740 |
| 42 | 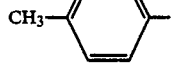 | 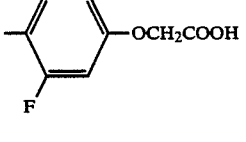 | 74%<br>118–120° C. (ethyl acetate-n-hexane)<br>IR $\nu_{max}^{nujol}$ (cm$^{-1}$): 1740 |

The properties of sodium salts:
  Example. No. 25: m.p. 226°–228.5° C.;
  Example. No. 26: m.p. 127°–131° C. (decomp.);
  Example. No. 32: m.p. 206°–207° C.;
  Example. No. 33: m.p. 226.5°–229° C.

EXAMPLE 43

A mixture of 1.56 g of methyl (±)-4-(2-aminopropyl)-phenoxyacetate hydrochloride, 48 ml of ethyl acetate, 2.07 g of potassium carbonate, 16 ml of water and 1.6 g of 4-nitrophenylsulfonyl chloride is stirred at room temperature overnight. The ethyl acetate layer is separated therefrom, dried, and evaporated under reduced pressure to remove the solvent. The residue is recrystallized from a mixture of ethyl acetate and n-hexane, whereby 2.14 g of methyl (±)-4-[2-(4-nitrophenyl)sulfonylaminopropyl]phenoxyacetate are obtained as pale yellow prism.

Yield 87%;
m.p. 127.5°–128° C.;
Mass (m/e): 408 (M+);
IR $\nu_{max}^{nujol}$ (cm$^{-1}$): 3320, 3280, 1740;
NMR (CDCl$_3$, δ): 1.21 (3H, d, J=6.4 Hz), 2.5–2.7 (2H, m), 3.3–3.7 (1H, m), 3.81 (3H, s), 4.58 (2H, s), 6.67 (2H, d, J=8.3 Hz), 6.91 (2H, d, J=8.3 Hz), 7.78 (2H, d, J=8.7 Hz), 8.22 (2H, d, J=8.7 Hz).

EXAMPLES 44 TO 51

The corresponding starting compounds are treated to the same manner as described in Example 43 to give the compounds shown in Table 8.

TABLE 8

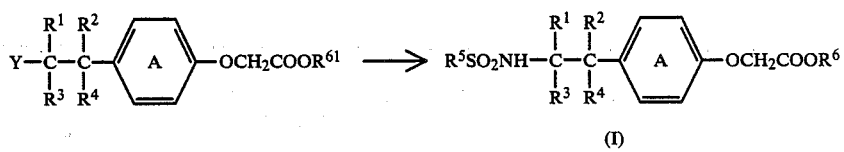

(I)

(Ring A = phenylene group, R$^1$ = H, R$^2$ = H, R$^6$ = CH$_3$, R$^{61}$ = CH$_3$, Y = NH$_2$)

| Ex. Nos. | R$^5$ | R$^3$ | R$^4$ | Compound (I) Yield M.p. (recrystallization solvent) IR |
|---|---|---|---|---|
| 44 | 4-NO$_2$-C$_6$H$_4$- | H | CH$_3$ | 94% 128.5–130.5° C. (isopropylether) IR $\nu_{max}^{nujol}$ (cm$^{-1}$): 3250, 1745 |
| 45 | 4-Br-C$_6$H$_4$- | CH$_3$ | H | 77% 115–116° C. (methanol-isopropylether-n-hexane) IR $\nu_{max}^{nujol}$ (cm$^{-1}$): 3260, 1750 |
| 46 | 2-Cl-C$_6$H$_4$- | H | CH$_3$ | 83%, oil IR $\nu_{max}^{neat}$ (cm$^{-1}$): 3320, 1760 |
| 47 | 2-Cl-C$_6$H$_4$- | CH$_3$ | H | 93%, oil IR $\nu_{max}^{neat}$ (cm$^{-1}$): 3310, 1760 |
| 48 | 2-CH$_3$-3-Cl-C$_6$H$_3$- | H | CH$_3$ | 94%, oil IR $\nu_{max}^{neat}$ (cm$^{-1}$): 3340, 1760 |
| 49 | 4-F-2-Cl-C$_6$H$_3$- | H | CH$_3$ | 86%, oil IR $\nu_{max}^{nujol}$ (cm$^{-1}$): 3320, 1755 |
| 50 | 4-CF$_3$-2-Cl-C$_6$H$_3$- | H | CH$_3$ | 90%, oil IR $\nu_{max}^{neat}$ (cm$^{-1}$): 3330, 1760 |

TABLE 8-continued

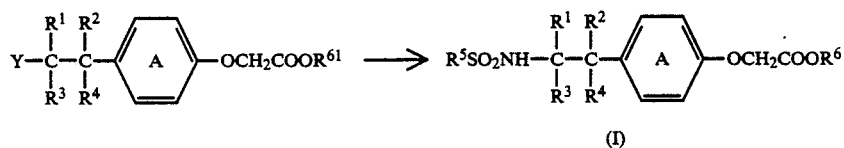

(I)

(Ring A = phenylene group, $R^1$ = H, $R^2$ = H, $R^6$ = $CH_3$, $R^{61}$ = $CH_3$, Y = $NH_2$)

| Ex. Nos. | $R^5$ | $R^3$ | $R^4$ | Compound (I) Yield M.p. (recrystallization solvent IR |
|---|---|---|---|---|
| 51 | Cl—⬡—Cl | H | $CH_3$ | 85%, oil IR $\nu_{max}^{nujol}$ (cm$^{-1}$): 3315, 1755 |

EXAMPLE 52

(1) 23.1 g of (±)-4-(2-acetylamino-1-methylethyl)-phenol are dissolved in 400 ml of acetone, and 19.9 g of methyl bromoacetate and 18 g of potassium carbonate are added thereto and the mixture is stirred overnight. 7.96 g of methyl bromoacetate and 7.2 g of potassium carbonate are further added thereto, and the mixture is stirred for 3 days. After the reaction, the mixture is evaporated under reduced pressure, and water is added to the residue. Then, the residue is extracted with ethyl acetate, washed with a saturated aqueous sodium chloride solution, dried and condensed to dryness, whereby 31.6 g of methyl (±)-4-(2-acetylamino-1-methylethyl)-phenoxyacetate are obtained as yellow oil.

Mass (m/e): 265 (M+);

IR $\nu_{max}^{nujol}$ (cm$^{-1}$): 3310, 1760, 1650.

(2) The product obtained above is dissolved in 200 ml of 6N-hydrochloric acid, and the solution is refluxed for 7.5 hours. After the reaction, the solvent is distilled off, and the residue is crystallized with tetrahydrofuran, whereby 19 g of (±)-4-(2-amino-1-methylethyl)phenoxyacetic acid hydrochloride are obtained as colorless solids.

m.p. 220.5°–223° C. (decomp.);
Mass (m/e): 209 (M+), 179;
IR $\nu_{max}^{nujol}$ (cm$^{-1}$): 1730.

(3) A mixture of 2.95 g of the product obtained above, 3.65 g of potassium carbonate, 30 ml of water and 2.45 g of 4-fluorophenylsulfonyl chloride is stirred at 80° C. for 2 hours. After cooling, the mixture is adjusted to pH 1 with 6N-hydrochloric acid, and extracted with ethyl acetate. The extract is condensed to dryness, and (±)-4-[2-(4-fluorophenyl)sulfonylamino-1-methylethyl)-phenoxyacetic acid obtained as the residue is treated with a 1N-aqueous sodium hydroxide solution to convert it to sodium salt. Then, said sodium salt is purified by chromatography on the column packed with HP-20, whereby 2.82 g of sodium (±)-4-[2-(4-fluorophenyl)sulfonylamino-1-methylethyl)phenoxyacetate are obtained as powder.

Yield: 60%;

m.p. 213°–214.5° C. (colorless prism, recrystallized from a mixture of water and isopropyl alcohol).

(4) 1.95 g of the product obtained above are dissolved in 30 ml of water, and adjusted to pH 1 with 10% hydrochloric acid. The mixture is extracted with chloroform. The chloroform extract is dried and evaporated to remove the solvent. The residue thus obtained is recrystallized from a mixture of ethyl acetate and n-hexane, whereby 1.65 g of (±)-4-[2-(4-fluorophenyl)sulfonylamino-1-methylethyl)phenoxyacetic acid are obtained as colorless prism.

Yield 90%;

m.p. 111.5°–114° C.;

H$^1$-NMR (CDCl$_3$, δ): 1.19 (3H, d, J=6.2 Hz), 2.6–3.3 (3H, m), 4.63 (2H, s), 6.6–7.3 (7H, m), 7.6–7.9 (2H, m);

IR $\nu_{max}^{nujol}$ (cm$^{-1}$): 3300, 1740;

Mass (m/e): 367 (M+).

EXAMPLES 53 TO 55

The corresponding starting compounds are treated in the same manner as described in Example 52 to give the compounds shown in Table 9.

TABLE 9

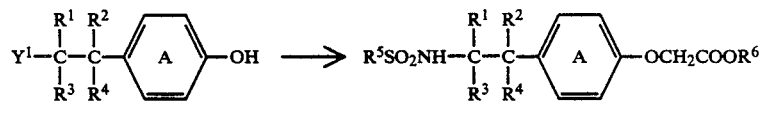

(Ring A = phenylene group, $R^1$ = H, $R^2$ = H, $R^6$ = H, $Y^1$ = NHCOCH$_3$)

| Ex. Nos. | $R^5$ | $R^3$ | $R^4$ | Compound (I) M.p. (recrystallization solvent IR |
|---|---|---|---|---|
| 53 | $CH_3$—⬡— | H | $CH_3$ | 133.5°–136° C. (decomp. ethyl acetate-n-hexane IR $\nu_{max}^{nujol}$ (cm$^{-1}$): 3270, 1740 |

TABLE 9-continued

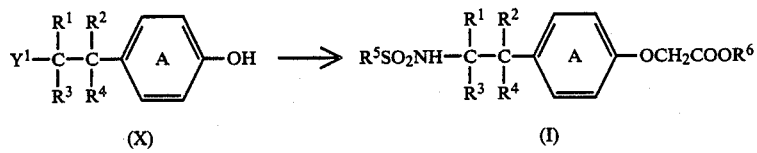

(Ring A = phenylene group, $R^1$ = H, $R^2$ = H, $R^6$ = H, $Y^1$ = NHCOCH$_3$)

| Ex. Nos. | $R^5$ | $R^3$ | $R^4$ | M.p. (recrystallization solvent) IR |
|---|---|---|---|---|
| 54 | Cl—⟨phenyl⟩— | H | CH$_3$ | 118°–119.5° C. (decomp. ethyl acetate-n-hexane) IR $\nu_{max}^{nujol}$ (cm$^{-1}$): 3263, 1740 |
| 55 | Br—⟨phenyl⟩— | H | CH$_3$ | 131°–133° C. (ethyl acetate-n-hexane) IR $\nu_{max}^{nujol}$ (cm$^{-1}$): 3280, 1750 |

EXAMPLE 56

A mixture of 2.95 g of (±)-4-(2-amino-1-methylethyl)phenoxyacetic acid hydrochloride, 3.82 g of sodium carbonate, 30 ml of water and 3.1 g of 2,5-dichlorophenylsulfonyl chloride is stirred at 80° C. for 3 hours. The reaction mixture is treated in the same manner as described in Example 43, whereby (±)-4-[2-(2,5-dichlorophenyl)sulfonylamino-1-methylethyl]phenoxyacetic acid is obtained.
M.p. 111.5°–116.5° C. (decomp.) (recrystallized from a mixture of ethyl acetate and n-hexane).
IR $\nu_{max}^{nujol}$ (cm$-1$): 3320, 1740, 1710
H$^1$-NMR (CDCl$_3$, δ): 1.20 (3H, d, J=6.4 Hz), 2.7–3.3 (3H, m), 4.65 (2H, s), 4.95 (1H, m), 6.82 (2H, d, J=9 Hz), 7.04 (2H, d, J=9 Hz), 7.3–7.5 (2H, m), 7.9–8.1 (1H, m).

EXAMPLE 57

(1) 1.98 g of 4-(2-amino-2-methylpropyl)phenol oxalate are suspended in 40 ml of methylene chloride, and 6.27 g of triethylamine and 6.5 g of 4-chlorophenylsulfonyl chloride are added thereto. The suspension is refluxed for 5 hours. After the reaction, the solvent is distilled off. The residue is dissolved in 50 ml of methanol, 35 ml of a 10% aqueous sodium hydroxide solution are added thereto, and the solution is refluxed for 40 minutes. The reaction solution is evaporated to remove the solvent, made acidic with 10% hydrochloric acid and extracted with ethyl acetate. The extract is washed with water, a dilute aqueous sodium bicabonate solution, and a saturated aqueous sodium chloride solution, successively. Then, the extract is dried and evaporated. The residue thus obtained is purified by silica gel column chromatography (solvent; chloroform, and chloroform:methanol=50:1), and recrystallized from a mixture of ethyl acetate and n-hexane, whereby 1.40 g of 4-[2-(4-chlorophenyl)sulfonylamino-2-methylpropyl]phenol are obtained as pale yellow prism.
Yield 53%;
m.p. 131.5°–133.5° C.;
Mass (m/e): 339 (M$^+$);
IR $\nu_{max}^{nujol}$ (cm$^{-1}$): 3450, 3310.

(2) 1.50 g of the product obtained above are dissolved in 20 ml of acetone, and 0.91 g of potassium carbonate is added thereto. A solution of 0.84 g of methyl bromoacetate in 20 ml of acetone is added thereto under stirring at room temperature, and the mixture is stirred for 24 hours. The reaction mixture is evaporated to remove the solvent, and the residue is dissolved in a mixture of ethyl acetate and water. The ethyl acetate solution is washed with water and a saturated aqueous sodium chloride solution, dried, and then evaporated to remove the solvent. Then, the residue obtained is recrystallized from a mixture of ethyl acetate and n-hexane, whereby 1.70 g of methyl (±)-4-[2-(4-chlorophenyl)sulfonylamino-2-methylpropyl]phenoxyacetate are obtained as pale yellow prism.
Yield 94%;
m.p. 133°–135° C.;
Mass (m/e): 411 (M$^+$);
IR $\nu_{max}^{nujol}$ (cm$^{-1}$): 3270, 1750, 1230;
H$^1$-NMR (CDCl$_3$, δ): 1.16 (6H, s), 2.78 (2H, s), 3.81 (3H, s), 4.52 (1H, s), 4.63 (2H, s), 6.85 (2H, d, J=8.8 Hz), 7.15 (2H, d, J=8.8 Hz), 7.41 (2H, d, J=9 Hz), 7.75 (2H, d, J=9 Hz).

(3) The product obtained above is treated in the same manner as described in Example 21 to give 4-[2-(4-chlorophenyl)sulfonylamino-2-methylpropyl]phenoxyacetic acid.
m.p. 177°–178° C. (recrystallized from a mixture of ethyl acetate and n-hexane);
Mass (m/e): 397 (M$^+$)
IR $\nu_{max}^{nujol}$ (cm$^{-1}$): 3300, 1730, 1710;
H$^1$-NMR (CDCl$_3$+DMSO-d$_6$, δ): 1.13 (6H, s), 2.79 (2H, s), 4.58 (2H, s), 5.67 (1H, s), 6.81 (2H, d, J=8.8 Hz), 7.16 (2H, d, J=8.8 Hz), 7.3–7.8 (4H, m).

EXAMPLES 58 TO 60

The corresponding starting compounds are treated in the same manner as described in Example 52-(1) and (2). The resulting free carboxylic acids are reacted with methanol to give the corresponding methyl esters thereof, which is then treated in the same manner as described in Example 21-(3). The compounds shown in Table 10 are thereby obtained.

TABLE 10

$$Y^1-\underset{\underset{R^3}{|}}{\overset{\overset{R^1}{|}}{C}}-\underset{\underset{R^4}{|}}{\overset{\overset{R^2}{|}}{C}}-\text{A}-\text{OH} \longrightarrow R^5SO_2NH-\underset{\underset{R^3}{|}}{\overset{\overset{R^1}{|}}{C}}-\underset{\underset{R^4}{|}}{\overset{\overset{R^2}{|}}{C}}-\text{A}-\text{OCH}_2\text{COOR}^6$$

(X)                                                            (I)

(Ring A = phenylene group, $R^1$ = H, $R^2$ = H, $R^6$ = H, $Y^1$ = NHCOCH$_3$)
Compound (I)

| Ex. Nos. | $R^5$ | $R^3$ | $R^4$ | M.p. (recrystallization solvent) IR optical rotation |
|---|---|---|---|---|
| 58 | 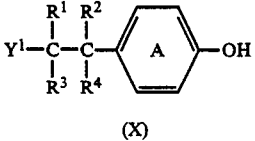 | H | CH$_3$ (−) | 99% 137°–138° C. (ethyl acetate-n-hexane) IR $\nu_{max}^{nujol}$ (cm$^{-1}$): 3280,1740 [α]$_D^{20}$ −8.63° (C = 1.019, methanol) |
| 59 | 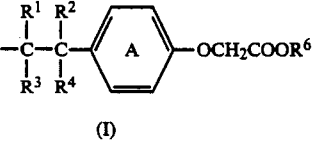 | H | CH$_3$ (+) | 95% 138°–139° C. (ethyl acetate-n-hexane) IR $\nu_{max}^{nujol}$ (cm$^{-1}$): 3280,1740 [α]$_D^{20}$ +8.92° (C = 1.008, methanol) |

$R^1$ = H, $R^2$ = CH$_3$, $R^3$ = H, $R^4$ = H, $R^7$ = OH, Y = NHCOCH$_3$)
Compound (I)

| Ex. No. | $R^5$ | 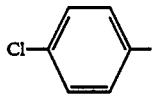—OCH$_2$COOR$^6$ | IR |
|---|---|---|---|
| 60 | 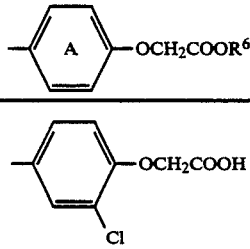 | 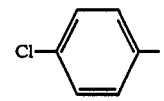 | 92%, oil IR $\nu_{max}^{neat}$ (cm$^{-1}$): 1740 |

EXAMPLE 61

(1) 6.76 g of (±)-1-(4-benzyloxy-3-methoxyphenyl)-2-aminopropane are dissolved in 120 ml of ethyl acetate, and a solution of 6.9 g of potassium carbonate in 60 ml of water is added thereto. A solution of 4.42 g of benzenesulfonyl chloride in 60 ml of ethyl acetate is added dropwise thereto, and the mixture is stirred for 45 minutes. The ethyl acetate layer is separated, dried and evaporated to remove the solvent, whereby 7.24 g of (±)-1-(4-benzyloxy-3-methoxyphenyl)-2-benzenesulfonylaminopropane are obtained as pale yellow oil.

(2) 7.16 g of the product obtained above are dissolved in 200 ml of tetrahydrofuran, and subjected to catalytic hydrogenation in the presence of 3 g of wet-10% palladiumcarbon at room temperature under an atmospheric pressure. After the reaction, the catalyst is filtered off, and the filtrate is evaporated to remove the solvent. The residual yellow oil is dissolved in 60 ml of acetone, and 3.61 g of potassium carbonate and a solution of 2.66 g of methyl bromoacetate in 60 ml of acetone are added thereto. The mixture is stirred overnight. After the reaction, acetone is distilled off, and water is added to the residue. The mixture is extracted with ethyl acetate. The ethyl acetate extract is washed with a saturated aqueous sodium chloride solution, dried and, evaporated to remove the solvent. The residual pale yellow oil is dissolved in 35 ml of methanol, 35 ml of a 1N-aqueous sodium hydroxide solution are added thereto, and the mixture is stirred for 1 hour. After the reaction, methanol is evaporated under reduced pressure. The residue is made acidic with hydrochloric acid and extracted with chloroform. The extract is dried and evaporated under reduced pressure to remove the solvent. Then, the residue is purified by silica gel column chromatography (solvent; chloroform:methanol=1000:1, 100:1, 10:1), whereby 4.06 g of (±)-2-methoxy-4-(2-benzenesulfonylaminopropyl)phenoxyacetic acid are obtained as oil.

Yield 62%;
Mass (m/e): 379 (M$^+$);
IR $\nu_{max}^{CHCl_3}$ (cm$^-$): 1730.

EXAMPLE 62

(1) (±)-1-(4-methoxy-3-methylphenyl)-2-aminopropane and benzenesulfonyl chloride are treated in the same manner as described in Example 61-(1) to give (±)-1-(4-methoxy-3-methylphenyl)-2-benzenesulfonylaminopropane.

(2) 11.48 g of the product obtained above are dissolved in 300 ml of methylene chloride and cooled at −60° C. 29.7 g of boron tribromide are added dropwise thereto under stirring, and the mixture is stirred at room temperature for 1 hour. The reaction mixture is cooled, decomposed with water and extracted with chloroform. After drying, the extract is evaporated to remove the solvent. The residual brown oil is dissolved in 320 ml of acetone, and 10.7 g of potassium carbonate and 7.89 g of methyl bromoacetate are added thereto. The mixture is stirred overnight. After the reaction, acetone is distilled off, and water is added to the residue. The mixture is extracted with ethyl acetate. The ethyl acetate extract is washed with a saturated aqueous sodium chloride solution, dried and evaporated to remove the solvent. The residue is dissolved in methanol, a 1N-aqueous sodium hydroxide solution is added thereto, and the mixture is stirred for 1 hour. After the reaction, methanol is distilled off, and the residue is purified by silica gel column chromatography (solvent; chloroform:methanol=1000:1, 100:1, 10:1), whereby 13.5 g of (±)-2-methyl-4-(2-benzenesulfonylaminopropyl)phenoxyacetic acid are obtained as oil.

Yield 72%;
Mass (m/e): 363 (M+);
IR $\nu_{max}^{CHCl_3}$ (cm$^{-1}$): 1730;

EXAMPLES 63 TO 67

The corresponding starting compounds are treated in the same manner as described in Example 62 to give the compounds shown in Table 11.

roform, and the mixture is stirred at room temperature overnight. The mixture is condensed to a volume of 1.1 liters, and refluxed for 3 hours. After cooling, the precipitated crystals are collected by filtration, washed and then dried. The colorless crystals thus obtained are added to a mixture of 750 ml of ethanol and 120 ml of conc. hydrochloric acid, and the mixture is refluxed for 50 minutes. After cooling, the precipitated crystals are collected by filteration, washed and then dried. 55.6 g of 2-amino-1-(4-benzyloxyphenyl)ethanone are obtained as colorless crystals.

Yield 67%;
M.p. 225° C. (decomp.);

(2) 1.11 g of the product obtained above are dissolved in a mixture of 10 ml of tetrahydrofuran and 5 ml of

TABLE 11

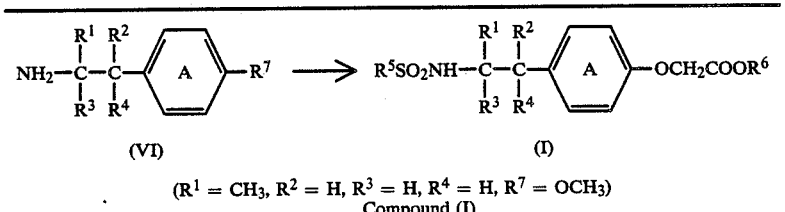

(VI) → (I)

($R^1$ = CH$_3$, $R^2$ = H, $R^3$ = H, $R^4$ = H, $R^7$ = OCH$_3$)
Compound (I)

| Ex. Nos. | R$^5$ | ![A]—OCH$_2$COOR$^6$ | M.p. (recrystallization solvent) |
|---|---|---|---|
| 63 | phenyl | CH$_3$ / —OCH$_2$COOH / CH$_3$ | 60%, oil<br>IR $\nu_{max}^{CHCl_3}$ (cm$^{-1}$): 1730 |
| 64 | phenyl | —OCH$_2$COOH / F | 62%<br>148°–150° C. (ethyl acetate-isopropylether-n-hexane)<br>IR $\nu_{max}^{nujol}$ (cm$^{-1}$): 1740 |
| 65 | Cl—phenyl | —OCH$_2$COOH / F | 72%<br>130.5°–132.5° C. (chloroform)<br>IR $\nu_{max}^{nujol}$ (cm$^{-1}$): 1720 |
| 66 | CH$_3$—phenyl | —OCH$_2$COOH / F | 77%<br>138°–141° C. (ethyl acetate-isopropylether<br>IR $\nu_{max}^{nujol}$ (cm$^{-1}$): 1740 |
| 67 | CF$_3$—phenyl | —OCH$_2$COOH / F | 74%<br>163°–164° C. (ethyl acetate-isoproplether)<br>IR $\nu_{max}^{nujol}$ (cm$^{-1}$): 1720 |

PREPARATION OF THE STARTING COMPOUNDS

Preparation 1

(1) 78 g of 1-(4-benzyloxyphenyl)-2-chloroethanone and 63 g of hexamine are dissolved in 2.2 liters of chloroform, and the mixture is stirred at room temperature water. A solution of 1.11 g of potassium carbonate in 10 ml of water and a solution of 1.41 g of benzenesulfonyl chloride in 10 ml of tetrahydrofuran are added dropwise thereto. The mixture is stirred at room temperature for 1.5 hours, and extracted with ethyl acetate. The ethyl acetate extract is washed, dried and evaporated to remove the solvent. The residue is recrystallized from ethyl acetate, whereby 1.34 g of 2-benzenesulfonylamino-1-(4-benzyloxyphenyl)ethanone are obtained as colorless needles.
Yield 89%;
m.p. 148°-149° C.;

(3) 4.37 g of magnesium are suspended in 180 ml of dried ether, and 4 drops of 1,2-dibromoethane are added thereto. After the mixture is stirred at room temperature for 30 minutes, a solution of 18.3 g of methyl iodide in 50 ml of ether is added dropwise thereto. A solution of 7.6 g of 2-benzenesulfonylamino-1-(4-benzyloxyphenyl)ethanone in 150 ml of tetrahydrofuran is added dropwise to said mixture under stirring and cooling. The mixture is stirred at room temperature overnight, and then refluxed for 2 hours. After cooling, a dilute aqueous ammonium chloride solution is added to the mixture, and the mixture is extracted with ethyl acetate. The extract is washed, dried and then evaporated under reduced pressure. The residue is purified by silica gel column chromatography (solvent; chloroform, and chloroform:methanol=50:1) and recrystallized from a mixture of ethyl acetate and n-hexane, whereby 4.92 g of 1-benzenesulfonylamino-2-(4-benzyloxyphenyl)-2-propanol are obtained as colorless crystals.
Yield 62%;
m.p. 150°-151° C.

Preparation 2

A tetrahydrofuran solution of 6.78 g of 1-(4-benzyloxy-3-methoxy-phenyl)-2-nitropropene is added dropwise to a suspension of 2.15 g of lithium aluminum hydride in tetrahydrofuran. The mixture is stirred at room temperature and then refluxed. After the reaction, excess lithium aluminum hydride is decomposed with ice water, and inorganic materials are filtered off. The filtrate is washed, dried and then condensed to dryness. 6 g of 1-(4-benzyloxy-3-methoxyphenyl)-2-aminopropane are obtained as pale yellow viscous oil.
Yield 97%.

Preparation 3

(1) A dimethoxyethane solution of 5.25 g of potassium tert-butoxide is added dropwise to a dimethoxyethane solution containing 3.93 g of 2-fluoro-4-methoxyacetophenone and 4.57 g of p-toluenesulonylmethylisocyanid. Said dropwise addition is carried out at a temperature below 10° C. After the reaction, the mixture is added to ice water, and extracted with ether. The extract is washed, dried and condensed to dryness. The residue is purified by silica gel column chromatography, whereby 3.83 g of 2-(2-fluoro-4-methoxyphenyl)-2-methylethanenitrile are obtained as colorless oil.
Yield 83%;
IR $\nu_{max}^{neat}$ (cm$^{-1}$): 2250

(2) 15 ml of Raney Nickel are added to an ethanol solution of 5.05 g of the product obtained above, and 30 g of hydrazine monohydrate are added dropwise thereto at a temperature between 40° and 50° C. After the reaction, the catalyst is filtered off, and the filtrate is evaporated. The residue is added to 15% methanolic hydrochloric acid, and the mixture is evaporated to remove the solvent. The residue is recrystallized from a mixture of methanol and isopropylether, whereby 4.23 g of 1-amino-2-(2-fluoro-4-methoxyphenyl)propane hydrochloride are obtained as colorless crystals.
Yield 75%;
m.p. 147°-149° C.

Preparation 4

The corresponding starting compounds are treated in the same manner as described in Preparation 3 to give 1-amino-2-(3-fluoro-4-methoxyphenyl)propane.
Yield 99%;
IR $\nu_{max}^{neat}$ (cm$^{-1}$): 3270.

Preparation 5

(1) 504 mg of 60% sodium hydride are added to tetrahydrofuran, and a solution of 2.47 g of triethylphosphonoacetate is added thereto under argon atmosphere. The mixture is stirred at room temperature. Then, a solution of 1.85 g of 3-chloro-4-methoxyacetophenone in tetrahydrofuran is added thereto, and the mixture is stirred at room temperature. After the reaction, water is added to the mixture, and the organic layer is separated therefrom. The aqueous layer is extracted with ethyl acetate. The organic solutions are combined and evaporated to remove the solvent. The residue is purified by silica gel column chromatography, whereby 1.47 g of ethyl 3-(3-chloro-4-methoxyphenyl)isocrotonate and 0.18 g of ethyl 3-(3-chloro-4-methoxyphenyl)crotonate are obtained.
ethyl 3-(3-chloro-4-methoxyphenyl)isocrotonate:
Yield 57.7%;
m.p. 67°-68° C.;
IR $\nu_{max}^{nujol}$ (cm$^{-1}$): 1700.
ethyl 3-(3-chloro-4-methoxyphenyl)crotonate:
Yield 7.1%;
oil;
IR $\nu_{max}^{neat}$ (cm$^{-1}$): 1710.

(2) 0.3 g of 10% palladium carbon is added to an acetic acid solution containing 1.41 g of ethyl 3-(3-chloro-4-methoxyphenyl)-isocrotonate, and the mixture is subjected to catalytic hydrogenation at room temperature under atmospheric pressure. After the reaction, the catalyst is filtered off, and the filtrate is condensed. Methanol and an aqueous sodium hydroxide solution are added to the residue, and the mixture is stirred. Then, the solvent is distilled off, and the residue is made acidic with hydrochloric acid. The aqueous mixture is extracted with ethyl acetate. The extract is washed with water, dried and then condensed to dryness. The residue is purified by silica gel column chromatography, and recrystallized from n-hexane, whereby 807 mg of 3-(3-chloro-4-methoxyphenyl)butyric acid are obtained as colorless oil.
Yield 64%;
m.p. 73.5°-75° C.

(3) A solution of 12.23 g of the product obtained above, 6.49 g of triethylamine and 17.66 g of diphenylphosphorylazide in toluene is stirred at room temperature and then refluxed. 11.58 g of benzylalcohol are added thereto, and the mixture is again refluxed. Ethyl acetate is added to the reaction mixture, and said mixture is washed, dried and then condensed to dryness. 17.85 g of 1-benzyloxycarbonylamino-2-(3-chloro-4-methoxyphenyl)propane are obtained as oil.
Yield 100%.

(4) 33 ml of an aqueous 25% hydrobromide-acetic acid solution are added dropwise to an acetic acid solution containing 16.42 g of the product obtained above. After stirring the mixture, ether is added thereto, and the precipitated crystals are collected by filtration. 10.33 g of 1-amino-2-(3-chloro-4-methoxyphenyl)propane hydrobromide are obtained.

Yield 78%;
m.p. 163.5°–165° C.

Preparation 6

A mixture of 4.64 g of (±)-4-(2-amino-1-methylethyl)phenol hydrobromide, 100 ml of ethyl acetate, 6.92 g of potassium carbonate, 40 ml of water and 3.75 g of benzyloxycarbonyl chloride is stirred at room temperature overnight. After the reaction, the ethyl acetate layer is separated therefrom, washed, dried, and then evaporated under reduced pressure to remove the solvent. 4.82 g of (±)-4-(2-benzyloxycarbonylamino-1-methylethyl)phenol are obtained as pale yellow oil.
Yield 85%;
Mass (m/e): 285(M+);
IR $\nu_{max}^{neat}$ (cm$^{-1}$): 3350, 1690.

Preparations 7 to 9

The corresponding starting compounds are treated in the same manner as described in Preparation 6 to give the compounds shown in Table 12.

TABLE 12

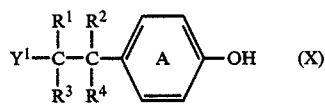 (X)

(R$^1$ = H, R$^2$ = H, Ring A = phenylene,

Y$^1$ = NHCOOCH$_2$ 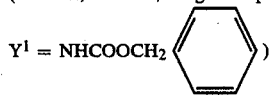 )

| Prep. Nos. | Compound (X) | | |
|---|---|---|---|
| | R$^3$ | R$^4$ | Yield M.p |
| 7 | CH$_3$ | H | 91% oil |
| 8 | C$_2$H$_5$ | H | 85% 126°–128° C. |
| 9 | H | C$_2$H$_5$ | 90% oil |

Preparation 10

(1) 4.19 g of 1-amino-2-(2-fluoro-4-methoxyphenyl)propane hydrochloride are neutralized with a mixture of chloroform and an aqueous sodium bicarbonate solution. The chloroform layer is separated therefrom and condensed to dryness. Hydrobromic acid is added to the residue, and the mixture is refluxed. Then, the reaction mixture is evaporated, and the residue is recrystallized from a mixture of isopropylalcohol and isopropylether. 4.53 g of 3-fluoro-4-(2-amino-1-methylethyl)phenol hydrobromide are obtained.
Yield 95%;
m.p. 182°–183.5° C.

(2) 2.9 g of benzyloxycarbonyl chloride are added to a solution of 4.47 g of the product obtained above in ethyl acetate-water containing sodium bicarbonate and the mixture is stirred at room temperature for 1 hour. After the reaction, the ethyl acetate layer is separated therefrom, washed and dried. Then, the ethyl acetate layer is condensed to dryness, whereby 5.82 g of 3-fluoro-4-(2-benzyloxycarbonylamino-1-methylethyl)phenol are obtained as oil.
Yield 100%;
IR $\nu_{max}^{neat}$ (cm$^{-1}$): 3330, 1690.

Preparation 11

1-amino-2-(3-fluoro-4-methoxyphenyl)propane hydrochloride is treated in the same manner as described in Preparation 10 to give 2-fluoro-4-(2-benzyloxycarbonylamino-1-methylethyl)phenol as colorless oil.
Yield 100%;
IR $\nu_{max}^{neat}$ (cm$^{-1}$): 3350, 1670.

Preparation 12

(1) A mixture of 19.8 g of (±)-1-amino-2-(4-methoxyphenyl) propane, 200 ml of ethyl acetate, 200 ml of water and 84 g of sodium bicarbonate is cooled at 5° to 10° C. under stirring, and 18.8 g of acetyl chloride in 100 ml of ethyl acetate are added dropwise thereto at the same temperature. After the reaction, the ethyl acetate layer is separated therefrom, washed, dried and then condensed to dryness under reduced pressure, whereby 24.8 g of (±)-1-acetylamino-2-(4-methoxyphenyl)propane are obtained as oil.
Mass (m/e): 207(M+);
IR $\nu_{max}^{neat}$ (cm$^{-1}$): 3290, 1650.

(2) The product obtained above is dissolved in 750 ml of methylene chloride. After cooling to −60° C., a methylene chloride solution of 69 g of boron tribromide is added dropwise thereto at the same temperature for 1.5 hours under stirring. After the mixture is stirred at room temperature, said mixture is again cooled to −50° to −60° C. Water and methylene chloride are added to the mixture. Then, the organic layer is separated therefrom, and washed with an aqueous sodium bicarbonate solution and a saturated aqueous sodium chloride solution. The aqueous layer are combined, neutralized with an aqueous sodium bicarbonate solution, and evaporated under reduced pressure. The resulting oily residue is extracted with ethyl acetate. The extract is dried, and evaporated under reduced pressure, whereby 23.1 g of (±)-4-(2-acetylamino-1-methylethyl)phenol are obtained as oil.
Yield 100%;
Mass (m/e): 193(M+);
IR $\nu_{max}^{neat}$ (cm$^{-1}$): 3290, 3020, 1655.

Preparations 13 to 15

The corresponding starting compounds are treated in the same manner as described in Preparation 12 to give the compounds shown in Table 13.

TABLE 13

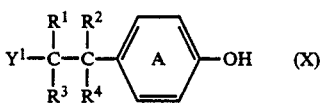

(R¹ = H, R³ = H, R⁴ = H, Y¹ =NHCOCH₃)
Compound (X)

| Prep. Nos. | R² | $-\langle A \rangle-OH$ | Yield M.p. |
|---|---|---|---|
| 13 | CH₃ (−) | 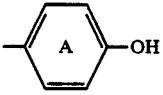 | 94% IR $\nu_{max}^{neat}$ (cm⁻¹): 3290,1650 [α]$_D^{20}$ −44.60° (C = 1.009, methanol) |
| 14 | CH₃ (+) | 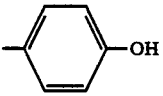 | used for subsequent reactions without isolation from the reaction solution |
| 15 | CH₃ | 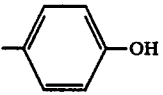 | 80%, oil IR $\nu_{max}^{neat}$ (cm⁻¹): 3300,3100,1650 |

What is claimed is:

1. A phenoxyacetic acid derivative of the formula:

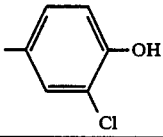

wherein Ring A is phenylene group or phenylene group having 1 or 2 substituent(s) selected from a lower alkyl group and a halogen atom; either one or two group(s) of R¹, R², R³ and R⁴ is/or are a lower alkyl group, and the other groups are hydrogen atom; R⁵ is phenyl group or a phenyl group having 1 or 2 substituent(s) selected from a lower alkyl group, a halogen atom, a lower alkoxy group, a trihalogenomethyl group and nitro group; and —COOR⁶ is carboxyl group or a protected carboxyl group or a pharmaceutically acceptable salt thereof.

2. The compound claimed in claim 1, in which Ring A is phenylene group or a phenylene group having 1 or 2 substituent(s) selected from an alkyl group of one to three carbon atoms and a halogen atom; either one or two group(s) of R¹, R², R³ and R⁴ is/or are an alkyl group of one to four carbon atoms, and the other groups are hydrogen; and R⁵ is phenyl group or a phenyl group having 1 to 2 substituent(s) selected from an alkyl group of one to three carbon atoms, a halogen atom, an alkoxy group of one to three carbon atoms, trihalogenomethyl group and nitro group.

3. The compound claimed in claim 2, in which Ring A is phenylene group or a phenylene group substituted with a halogen atom; either one of R¹ to R⁴ is an alkyl group of one to four carbon atoms, and the other groups of R¹ to R⁴ are hydrogen atom; and R⁵ is phenyl group or a phenyl group having a substituent selected from an alkyl group of one to three carbon atoms, a halogen atom, trihalogenomethyl group and nitro group.

4. The compound claimed in claim 3, in which Ring A is phenylene group or a phenylene group having a substituent selected from fluorine atom and chlorine atom; either one of R¹ to R⁴ is methyl group or ethyl group, and the other groups are hydrogen atom; and R⁵ is phenyl group or a phenyl group having a substituent selected from methyl group, fluorine atom, chlorine atom, bromine atom, trifluoromethyl group and nitro group.

5. The compound as claimed in claim 4, in which R⁵ is phenyl group, 4-fluorophenyl group, 4-chlorophenyl group, 4-bromophenyl group, 4-methylphenyl group, 4-trifluoromethylphenyl group, or 4-nitrophenyl group.

6. The compound as claimed in claim 5, in which Ring A is phenylene group or a phenylene group substituted with fluorine atom.

7. The compound as claimed in claim 6, in which Ring A is phenylene group; and R⁵ is 4-chlorophenyl group.

8. The compound as claimed in claim 7, in which either one of R¹ and R³ is methyl group or ethyl group, and the other group is hydrogen atom; R² and R⁴ are hydrogen atom.

9. The compound as claimed in any one of claims 1-4, in which —COOR⁶ is free carboxyl group, or a pharmaceutically acceptable salt thereof.

10. The compound claimed in claim 5, which is selected from:
4-[2-(4-chlorophenyl)sulfonylaminopropyl]phenoxyacetic acid,
4-[2-(4-chlorophenyl)sulfonylamino-1-methylethyl]-phenoxyacetic acid,
4-[2-(4-bromophenyl)sulfonylamino-1-methylethyl]-phenoxyacetic acid,
4-(2-benzenesulfonylaminopropyl)-2-fluorophenoxyacetic acid,
4-[2-(4-chlorophenyl)sulfonylaminopropyl]-2-fluorophenoxyacetic acid, 4-[2-(4-trifluoromethylphenyl)sulfonylaminopropyl]-2-fluorophenoxyacetic acid,
4-[2-(4-methylphenyl)sulfonylaminopropyl]-2-fluorophenoxyacetic acid,
4-[2-(4-nitrophenyl)sulfonylaminopropyl]phenoxyacetic acid,
4-[2-(4-chlorophenyl)sulfonylaminobutyl]phenoxyacetic acid,
4-(2-benzenesulfonylamino-1-methylethyl)-2-fluorophenoxyacetic acid,
4-(2-benzenesulfonylamino-1-methylethyl)-3-fluorophenoxyacetic acid,
4-[2-(4-methylphenyl)sulfonylamino-1-methylethyl]phenoxyacetic acid,
4-[2-(4-methylphenyl)sulfonylamino-1-methylethyl]-2-fluorophenoxyacetic acid,
4-[2-(4-fluorophenyl)sulfonylamino-1-methylethyl]phenoxyacetic acid,
4-[2-(4-chlorophenyl)sulfonylamino-1-methylethyl]-2-fluorophenoxyacetic acid,
4-[2-(4-chlorophenyl)sulfonylamino-1-methylethyl]-2-chlorophenoxyacetic acid,
4-[2-(4-trifluoromethylphenyl)sulfonylamino-1-methylethyl]phenoxyacetic acid,
4-[2-(4-chlorophenyl)sulfonylamino-1-ethylethyl]phenoxyacetic acid,
or a pharmaceutically acceptable salt thereof.

11. The compound as claimed in claim 8, which is 4-[2-(4-chlorophenyl)sulfonylaminopropyl]phenoxyacetic acid, or a pharmaceutically acceptable salt thereof.

12. The compound as claimed in claim 8, which is (−)-4-[2-(4-chlorophenyl)sulfonylaminopropyl]phenoxyacetic acid, or a pharmaceutically acceptable salt thereof.

13. A pharmaceutical composition which comprises an effective amount of the compound claimed in any one of claims 1, 7 or 11 and a pharmaceutically acceptable carrier therefor.

14. A method for prophylaxis or treatment of a thrombotic disease in a warm-blooded animal which comprises administering to said warm-blooded animal an effective amount of the compound claimed in any one of claims 1, 7 or 11.

* * * * *